US005317236A

United States Patent [19]
Zavracky et al.

[11] Patent Number: 5,317,236
[45] Date of Patent: May 31, 1994

[54] SINGLE CRYSTAL SILICON ARRAYED DEVICES FOR DISPLAY PANELS

[75] Inventors: Paul M. Zavracky, Norwood; John C. C. Fan, Chestnut Hill; Robert McClelland, Norwell, all of Mass.; Jeffrey Jacobsen, Hollister, Calif.; Brenda Dingle, Norton; Mark B. Spitzer, Sharon, both of Mass.

[73] Assignee: Kopin Corporation, Taunton, Mass.

[21] Appl. No.: 815,684

[22] Filed: Dec. 31, 1991

Related U.S. Application Data

[63] Continuation-in-part of Ser. No. 636,602, Dec. 31, 1990, Pat. No. 5,206,749.

[51] Int. Cl.[5] ............................................. H01J 9/00
[52] U.S. Cl. ................................. 315/169.3; 445/1; 437/21; 437/29; 437/84; 437/173; 437/974; 148/DIG. 135
[58] Field of Search ................. 445/1; 437/19, 21, 40, 437/29, 83, 84, 173, 974; 148/DIG. 135; 315/169.3

[56] References Cited

U.S. PATENT DOCUMENTS

| | | | |
|---|---|---|---|
| 3,807,037 | 4/1974 | Fischer | 437/84 |
| 3,869,646 | 3/1975 | Kirfon et al. | 315/246 |
| 3,904,924 | 9/1975 | Hilsum et al. | 315/169.3 |
| 3,947,842 | 3/1976 | Hilsum et al. | 340/324 R |
| 3,972,040 | 7/1976 | Hilsum et al. | 340/324 R |
| 4,127,792 | 11/1978 | Nakata | 313/500 |
| 4,137,481 | 1/1979 | Hilsum et al. | 313/503 |
| 4,143,297 | 3/1979 | Fischer | 313/502 |
| 4,266,223 | 5/1981 | Frame | 340/719 |
| 4,399,015 | 8/1983 | Endo et al. | 204/192 |
| 4,409,724 | 10/1983 | Tasch, Jr. et al. | 437/83 |
| 4,717,606 | 1/1988 | Hale | 428/1 |
| 4,797,667 | 6/1989 | Dolinar et al. | 340/781 |
| 4,852,032 | 7/1989 | Matsuda et al. | 364/708 |
| 4,929,884 | 5/1990 | Bird et al. | 323/313 |
| 4,977,350 | 12/1990 | Tanaka et al. | 313/505 |
| 4,980,308 | 12/1990 | Hayashi et al. | 437/83 |

FOREIGN PATENT DOCUMENTS

0151508 8/1985 European Pat. Off. .
61-199243 8/1986 Japan .
62-195581 8/1987 Japan .
WO88/09268 12/1988 PCT Int'l Appl. .

OTHER PUBLICATIONS

International Search Report, International Application No.: PCT/US91/09770, Filed Dec. 31, 1991.
Color Electroluminescent Display Development, James Hurd, Planar Systems, Inc. Flat Information Display-1990.
High Luminance White El Device For Color Flat Panels, Katsuzo Kaminishi, Oki Electric Industry Company, Flat Information Display-1990.
Proceedings of The Fourth International Symposium on Silicon-On-Insulator Technology and Devices, Dennis N. Schmidt, Motorila, Inc.
Vanfleteren, J., "Design of a Prototype Active Matrix CdSe TFT Addressed Laboratory of Electronics Lohja-Finlux El Display", Ghent State University, Belgium & Olarinluoma Finland, pp. 216-219.

(List continued on next page.)

Primary Examiner—Robert J. Pascal
Assistant Examiner—Michael Shingleton
Attorney, Agent, or Firm—Hamilton, Brook, Smith & Reynolds

[57] ABSTRACT

A display panel is formed using a single crystal thin-film material that may be transferred to substrates for display fabrication. Pixel arrays form light valves or switches that can be fabricated with control electronics in the thin-film material prior to transfer. The resulting circuit panel is then incorporated into a display panel with a light emitting or liquid crystal material to provide the desired display.

28 Claims, 25 Drawing Sheets

OTHER PUBLICATIONS

Harkonen, G. et al., "A 9 Inch Diagonal, Compact, Multicolor TFEL Display", 1991 International Display Research Conference, CH/3071-8/91/0000-00-43-0044.

Morton, C. et al., "Effects of Bulk Space Charge on the Current Luminescence Characteristics of ZnS:Mn ACTFEL Display of Devices" 1991 International Display Research Conference, CH-3071-8/91/0000-0130-0132.

Vanfletern, J. et al., "Evaluation of a 64×64 CdSe TFT Addressed ACTFEL Display Demonstrator", 1991 International Display Research Conference, CH-3071-8/91/0000-0134-0136.

Tanaka, S. et al., "Luminance Improvement of Blue- and White-Emitting Srs TFEL Devices by Annealing in Ar-S Atmosphere" 1991 International Display Research Conference, CH-3071-8/91/0000-0137-0142.

⟨or⟩

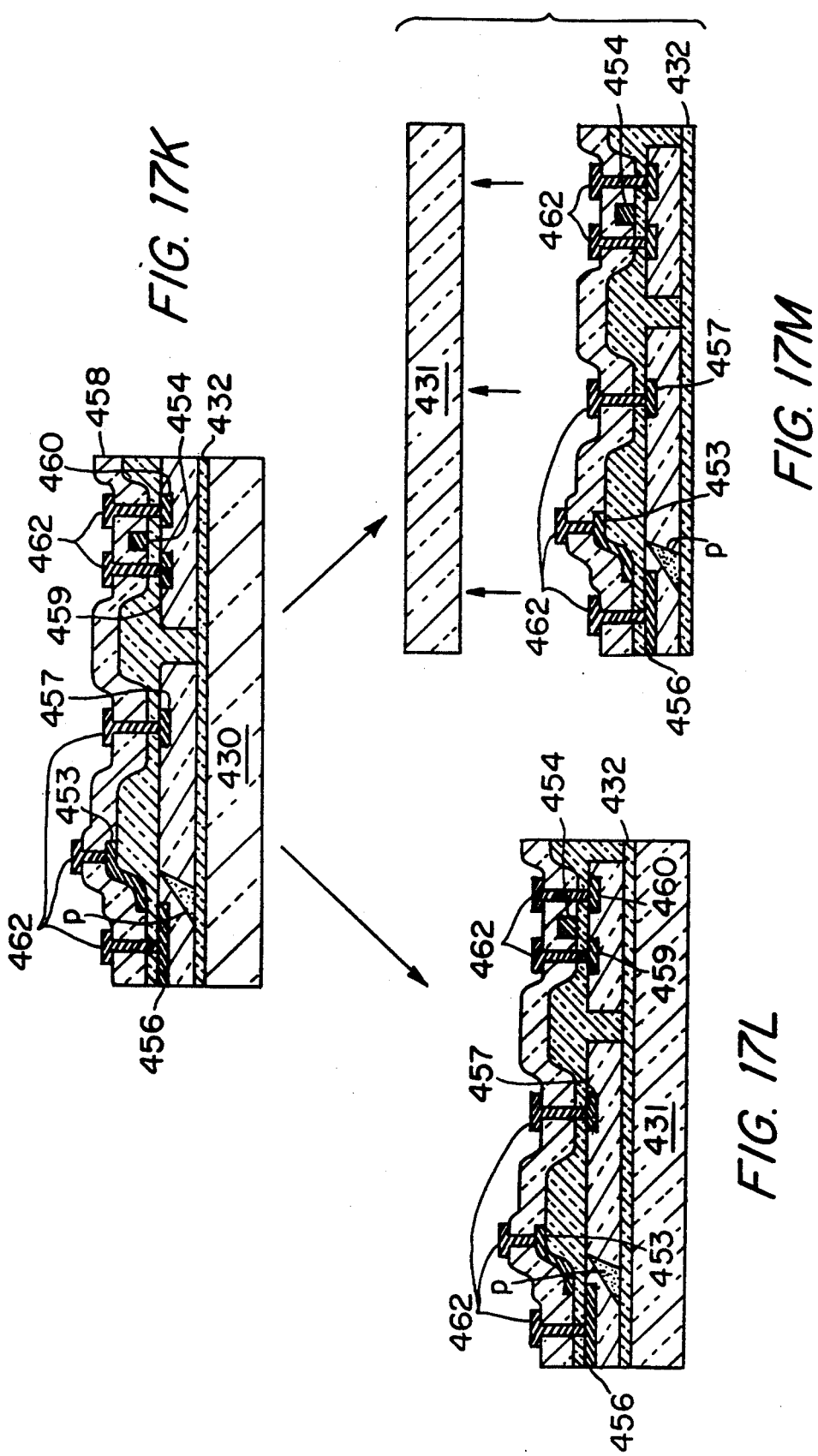

SINGLE CRYSTAL SILICON ARRAYED DEVICES FOR DISPLAY PANELS

RELATED APPLICATION

This document is a continuation-in-part of U.S. patent application, Ser. No. 07/636,602 filed Dec. 31, 1990 now U.S. Pat. No. 5,206,749.

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture. The most promising route to large scale high quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent grey scale that can be attained with TFT-compatible LCDs.

Flat panel displays employing LCD's generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across it between the circuit panel and a ground affixed to the filter plate. Thus, when a particular pixel of the display is turned on, the liquid crystal material rotates polarized light being transmitted through the material so that it will pass through the second polarizing filter.

The primary approach to TFT formation over the large areas required for flat panel displays has involved the use of amorphous silicon which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus, the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass which generally restricts further circuit processing to low temperatures.

An active matrix comprising TFTs is also useful in electroluminescent (EL) displays. The TFTs can be formed from silicon; however, the same factors that limit the use of polycrystalline silicon and amorphous silicon in the LCD active matrix also limit the use of these types of silicon in EL displays. Moreover, EL displays require TFTs capable not only of high speed and low leakage, but also of supporting the voltage level needed for electroluminescence.

Thus, a need exists for a method of forming high quality TFTs at each pixel of a panel display having the desired speed and providing for ease and reduced cost of fabrication. Further, a need exists for a method of forming high quality TFTs at each pixel of an EL panel display having the desired speed and providing for ease and reduced cost of fabrication, as well has providing the facility to operate the display pixels at the voltages necessary for luminescence.

SUMMARY OF THE INVENTION

The present invention relates to panel displays and methods of fabricating such displays using thin-films of essentially single crystal silicon in which transistors are fabricated to control each pixel of the display. For a preferred embodiment, the thin-film or transistor array is transferred onto an optically transmissive substrate such as glass or transparent organic films. In this embodiment, the thin-film single crystal silicon is used to form a pixel matrix array of thin-film transistors which actuate each pixel of an LCD. CMOS circuitry that is highly suitable for driving the panel display can be formed in the same thin-film material in which the transistors have been formed. The circuitry is capable of being fully interconnected to the matrix array using thin-film metallization techniques without the need for wires and wirebonding.

Each transistor, by application of an electric field or signal, serves to control the optical transmission of light from or through an adjacent material or device. For the purposes of this application the transistor and the adjacent material or device through which light from a source is transmitted is refered to as a light valve. Thus, each pixel of the panel display can be an independently controlled light valve. Examples of such light valves include LCDs or any liquid or solid state material whose light transmitting characteristics can be altered with an electric field or signal and which can be configured to provide a dense pixel array. The present devices and related methods of fabrication satisfy all of the requirements of large scale flat panel to produce highly defined color images. The transistors or switches can be paired with electroluminescent display elements (ELDs) or light emitting diodes (LEDs) to provide a display.

A preferred embodiment of the present invention utilizes large area semiconductor films, separates the films from the processing substrate, and mounts them on glass or other suitable optically transmissive materials. Films of single crystal silicon with thicknesses on the order of 2 microns or less, have been separated from epitaxial substrates, and the films have been mounted on glass and ceramics. Functional p-n junction devices such as field effect transistors ("FETs") are at least partially fabricated prior to separation and then transferred to glass. Various bonding procedures can be used for mounting on substrates including adhesives, electrostatic bonding, Van der Waal's forces or a eutectic alloy for bonding. Other known methods can also be utilized.

A preferred embodiment of the process comprises the steps of forming a thin essentially single crystal Si film on a release substrate, fabricating an array of pixel electrodes and thin-film enhancement mode transistors, and associated CMOS circuitry on the thin film. Each transistor is electrically connected to one of the pixel electrodes such that each pixel can be independently actuated by one of the transistors. The CMOS circuitry can be used to control pixel actuation and the resulting image or images that are displayed. Device fabrication can be initiated while the thin-film is still attached to the release substrate by formation of source, drain, channel and gate regions, and interconnection with pixel electrodes. By substantially completing device processing prior to transfer to the final panel substrate, a low temperature glass or polymer can be used. Alternatively, all or a portion of device fabrication can occur after release, or upon transfer of the processed film to the glass or plastic plate. After transfer, integration with color filters and liquid crystal materials completes the panel for an embodiment employing an LCD.

Preferred methods of thin-film formation processes employ silicon-on-insulator (SOI) technology where an essentially single crystal film is formed on an insulating substrate from which it can be released. For the purposes of the present application, the term "essentially single crystal" means a film in which a majority of crystals extend over a cross-sectional area, in the plane extending laterally through the film, of at least 0.1 cm$^2$ and preferably in the range of 0.5–1.0 cm$^2$ or more. Such films can be formed using known techniques, on sapphire, SiO$_2$, Si wafers, carbon and silicon carbide substrates, for example.

SOI technology generally involves the formation of a silicon layer whose crystal lattice does not match that of the underlying substrate. A particular preferred embodiment uses Isolated Silicon Epitaxy (ISE) to produce a thin film of high quality Si on a release layer. This process can include the deposition of a non-single crystal material such as amorphous or polycrystalline silicon on the release layer which is than heated to crystallize the material to form an essentially single crystal silicon. The use of a release layer enables the film and circuit release using oxides beneath the active layer that can be etched without harm to the circuits.

In a preferred embodiment the entire substrate on which the epitaxial film has been formed is removed by an etch back procedure.

Alternatively, methods of chemical epitaxial lift-off, a process for transferring semiconductor material to glass or other substrates, can be applied to large area sheets of the desired semiconductor material. These or other release methods can be used to remove any thin-film single crystal material from a growth substrate for transfer onto substrates for circuit panel fabrication.

The present invention includes CMOS circuit and pixel electrode formation in a recrystallized silicon film that is then, secured to a second transfer substrate, removed from the starting wafer or substrate, and mounted on the glass or other suitable substrate to form the circuit panel. Alternatively, one can first form the circuits, bond the circuits to glass, and then separate the circuits from the substrate. The pixels are positioned in rows and columns having a planar geometry. The order of the fabrication steps allows the use of conventional fast CMOS (or other) logic onboard the glass, since the high temperature processing for these circuits are performed prior to transfer.

Another preferred embodiment involves the fabrication of a discrete array of transistor elements, transferring these elements onto a stretchable substrate which either contracts or expands to provide the desired spacing or registration of the discrete elements and then transferring these elements onto a final substrate that is including in the display panel.

Yet another preferred embodiment of the present invention relates to electroluminescent (EL) panel displays and methods of fabricating such displays using single crystal silicon materials. Single crystal silicon is preferred for achieving high resolution in a small (6in×6in or less) active matrix EL display. In an EL display, one or more pixels are energized by alternating current (AC) which must be provided to each pixel by row and column interconnects. The efficient conduction of AC by the interconnects is limited by parasitic capacitance. The use of an active matrix, however, provides a large reduction of the interconnect capacitance and can enable the use of high frequency AC to obtain more efficient electroluminescence in the pixel phosphor and hence increased brightness. In accordance with the present invention, the TFTs that provide this advantage are formed in a single crystal wafer, such as bulk Si wafers, or thin-films of single crystal or essentially single crystal silicon. These high quality TFTs are employed in an EL panel display, providing high speed and low leakage as well as supporting the high voltage levels needed for electroluminescence.

Existing EL displays provide a low brightness output because passive circuitry for exciting pixel phosphors typically operates at a pixel excitation frequency (about 100 Hz) that is low relative to the luminance decay time of the phosphor material. In an EL display of the present invention, the TFTs are formed in an active matrix using bulk or thin film single or essentially single crystal silicon characterized by its high carrier mobility. As such, the TFTs can operate at high switching speeds. Thus, the active matrix circuit panel employing high speed TFTs co-located with the pixels can provide a high phosphor excitation frequency relative to the luminance decay time of the phosphor material resulting in increased brightness of the display. An EL display of the present invention is capable of providing a phosphor excitation frequency of 1000–10,000 Hz. Preferably, the EL display of the present invention provides a phosphor excitation frequency of more than about 5000 Hz and up to about 10,000 Hz leading to a proportionate increase in luminance.

In preferred embodiments, a thin layer of single crystal silicon is used to form a circuit panel comprising an array of transistors and an array of pixel electrodes, each pixel electrode being actuatable by one or more transistors. An electroluminescent material is positioned adjacent to the circuit panel and patterned to form an array of EL elements. For the EL display embodiments, each transistor (or transistor circuit), the associated pixel electrode and the associated EL material element are referred to as a pixel. As such, the EL display is comprised of a plurality of independently controllable pixels. For each pixel, the transistor (or transistor circuit), being capable of generating an electric field or signal across the adjacent EL material material, serves to control the emission of light by the EL material.

CMOS drive circuitry suitable for driving the EL panel display may be formed in the same single crystal material in which matrices of high voltage DMOS transistors and pixel electrodes have been formed. The drive circuitry is capable of being fully interconnected to the matrix of pixels using thin-film metallization techniques without the need for wires and wirebonding. Further, an optically transmissive electrode array is positioned over the electroluminescent material such that the electric field generated at each pixel lies between the optically transmissive electrode and the pixel electrode. As such, each pixel of the EL panel display can be an independently controlled light emitter whose light emitting properties are altered by the electric field or signal.

The present invention comprises devices and related methods for fabricating EL panel displays satisfying the requirements for producing high definition color images. To that end, the electroluminescent material is used to provide a pixel that is capable of producing a plurality of different wavelengths of light. More specifically, the electroluminescent material can comprise a plurality of patterned layers, each layer being capable of producing light of a particular wavelength which is different relative to the wavelengths produced by other layers when subjected to the electric field.

A preferred embodiment of the EL display formation process comprises the steps of forming a thin-film of single crystal silicon on a supporting substrate, forming an array of pixel electrodes, transistors and drive circuitry in or on the silicon film and forming an electroluminescent structure within each pixel adjacent to the silicon film. Each transistor is electrically connected to a pixel electrode such that each pixel may be independently actuated by a drive circuit.

Preferred methods of single crystal silicon layer formation processes for an EL display comprise SOI technology which involves the formation of a silicon layer on an insulating oxide on a substrate. SOI structures are preferred because they support the high voltage, high density circuitry of the EL display of the present invention. More specifically, the oxide layer allows the structure to sustain high voltage devices such as DMOS transistors. Further, the SOI structure can provide channel isolation for acheiveing higher density pixel circuitry which leads to a higher resolution display.

Other preferred methods relate to thin-film formation processing for the EL display involving SOI technology in which a single crystal silicon film is formed on a support substrate from which it can be separated and adhered to another material. In one preferred process, a film of single crystal silicon is formed on a substrate and active matrix circuitry is formed in the silicon film. Next, the film is separated from its substrate and transferred onto a reflective material for improving light emission of the pixels. In another preferred embodiment, the film is separated from its substrate and transferred onto a curved surface of a material for improved optical properties. For example, an EL display can be mounted upon a curved visor of a helmet-mounted system. Alternatively, the EL display may be mounted onto a curved windshield for a heads-up display.

In another preferred embodiment, a film of single crystal silicon is formed on a substrate and the entire wafer is then attached to a superstrate. Next, the entire substrate is removed by an etch back procedure.

A particular preferred method of the EL display formation process uses ISE which comprises the steps of forming a thin essentially single crystal Si film which includes forming a layer of polycrystalline silicon on an insulating substrate, forming a capping layer over the polycrystalline silicon and scanning the polycrystalline layer with a heat source to recrystallize the layer and form a wafer of substantially single crystal silicon. The display formation process further comprises the steps of forming an array of pixel electrodes, transistors and drive circuitry in the silicon film and forming an electroluminescent structure within each pixel. Each transistor is electrically connected to a pixel electrode such that each pixel may be independently actuated by one transistor circuit. The drive circuitry may be used to control pixel actuation and the resulting images are displayed.

The above, and other features of the invention including various novel details of construction and combination of parts, will now be more particularly described with reference to the accompanying drawings and that pointed out in the claims. It will be understood that the particular panel display and the methods used in fabricating those panels which embody the invention are shown by way of illustration only and not as a limitation of the invention. The principal features of this invention can be employed in various embodiments without departing from the scope of the invention.

BRIEF DESCRIPTION OF THE DRAWINGS

FIGS. 17A–17M is a preferred process flow sequence illustrating the fabrication of a circuit panel for an electroluminescent panel display.

DETAILED DESCRIPTION OF PREFERRED EMBODIMENTS

Figure 1A:
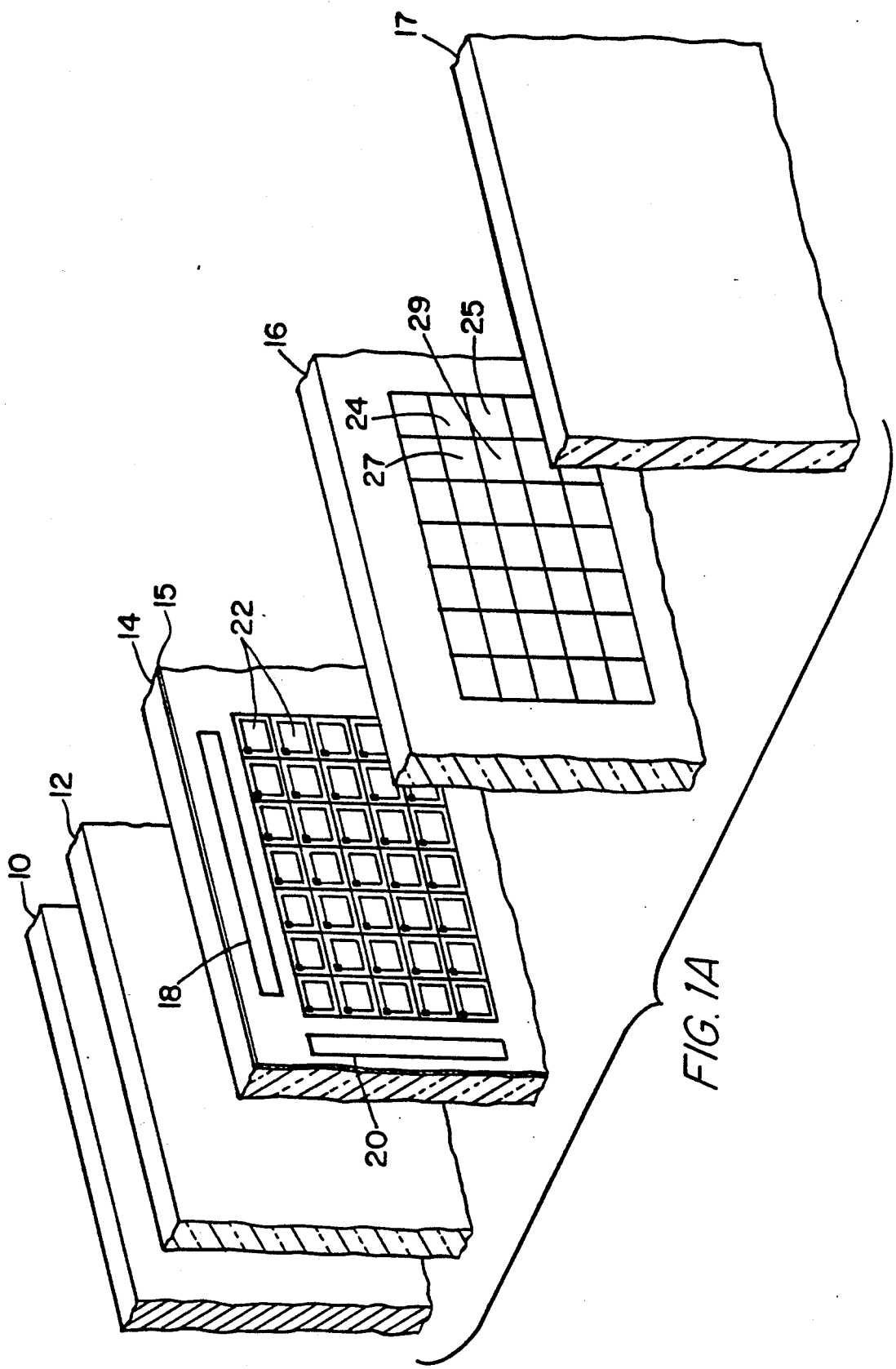
FIG. 1A is an exploded perspective view of a flat panel display in accordance with the invention.

A preferred embodiment of the invention is illustrated in the perspective view of a panel display in FIG. 1. The basic components of the display include a light source 10 that can be white or some other appropriate color, a first polarizing filter 12, a circuit panel 14, a filter plate 16 and a second polarizing filter 17, which are secured in a layered structure. A liquid crystal material (not shown) is placed in a volume between the circuit panel 14 and the filter plate 16. An array of pixels 22 on the circuit panel 14 are individually actuated by a drive circuit having first 18 and second 20 circuit components that are positioned adjacent the array such that each pixel can produce an electric field in the liquid crystal material lying between the pixel and a counterelectrode secured to the color filter plate 16. The electric field causes a rotation of the polarization of light being transmitted across the liquid crystal material that results in an adjacent color filter element being illuminated. The color filters of filter plate system 16 are arranged into groups of four filter elements such as blue 24, green 25, red 27, and white 29. The pixels or light valves associated with filter elements 24, 25, 27, 29 can be selectively actuated to provide any desired color for that pixel group.

The present invention employs any transmissive or emissive material to form each pixel of the display panel. To that end, some preferred embodiments employ the use of any liquid, such as the aforementioned liquid crystal material, to form a transmissive light valve for each pixel. Other preferred embodiments employ the use of a solid state material such as a ferroelectric material to form a transmissive light valve for each pixel. Further, other preferred embodiments employ the use of other solid state materials to form a light emitter for each pixel. An electroluminescent film, porous silicon or any light emitting material whose optical transmission properties can be altered by the application of an electric field can be used to form the light emitter. Accordingly, electroluminescent display elements (ELD), porous silicon display elements or light emitting diodes can be formed and used to provide a display.

Figure 1B:
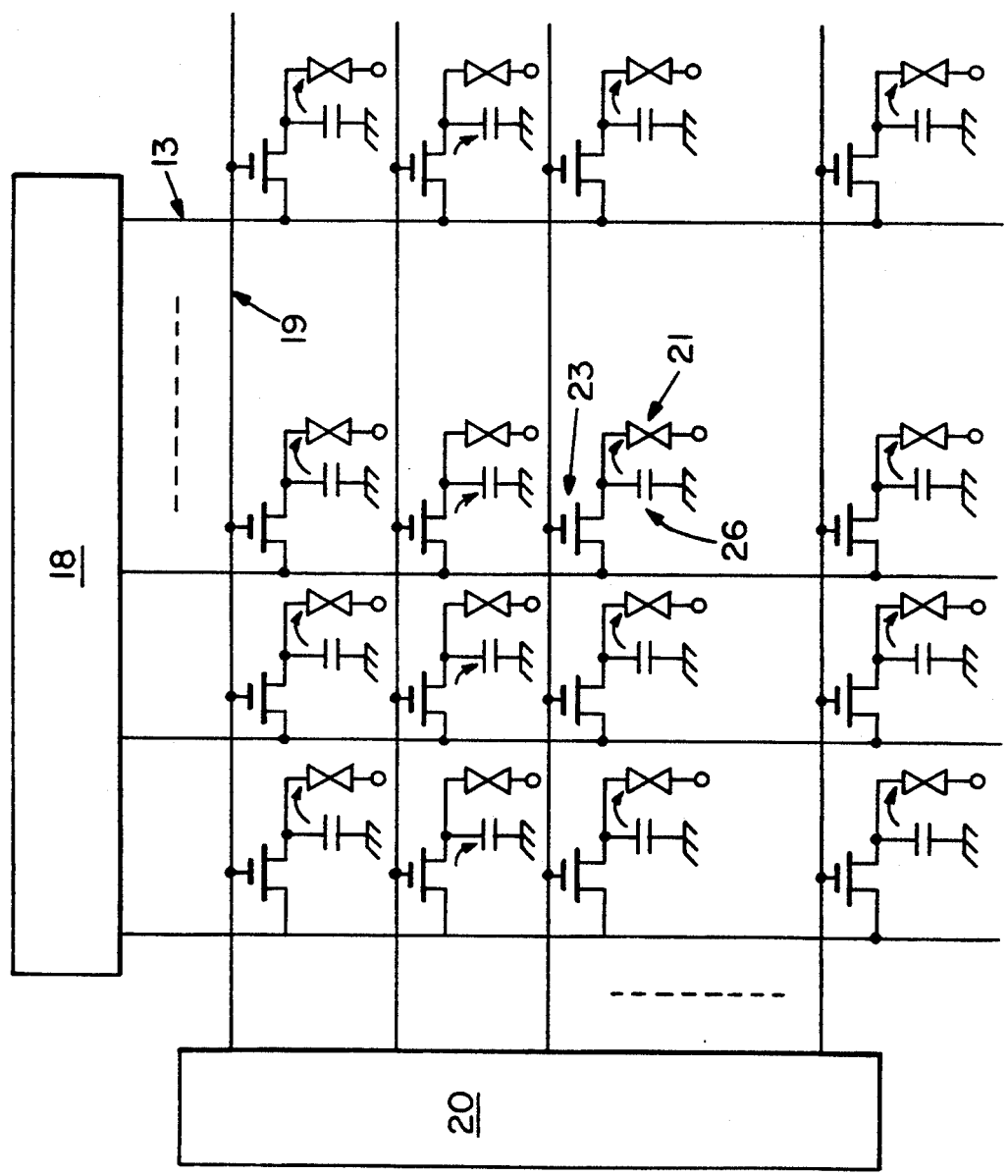
FIG. 1B is a circuit diagram illustrating the driver system for a preferred embodiment of the invention.

A drive circuit that can be used to control the display on the panel is illustrated in FIG. 1B. Circuit 18 receives an incoming signal and sends a signal to the pixels through buses 13. Circuit 20 will scan through buses 19 to turn on the individual transistors 23 which charges capacitor 26 in each pixel. The capacitor 26 sustains the charge on the pixel electrode and the liquid crystal 21 until the next scan of the array. The various embodiments of the invention may, or may not, utilize capacitors with each pixel depending upon the type of display desired.

FIGS. 2A–2L illustrate the use of an Isolated Silicon Epitaxy (ISE) process, to form silicon-on-insulator (SOI) films in which circuit panel circuitry is formed. Note that any number of techniques can be employed to provide a thin-film of single crystal Si. An SOI structure, such as that shown in FIG. 2A, includes a substrate 30 and an oxide 34 (such as, for example, $SiO_2$) that is grown or deposited on the substrate 30. A thin single crystal layer of silicon is formed over the oxide 34. The oxide (or insulator) is thus buried beneath the Si surface layer. For the case of ISE SOI structures, the top layer is a substantially single-crystal recrystallized Silicon, from which CMOS circuits can be fabricated. The use of a buried insulator provides devices having higher speeds than can be obtained in conventional bulk (Czochralski) material. Circuits containing in excess of 1.5 million CMOS transistors have been successfully fabricated in ISE material.

Figure 2A:
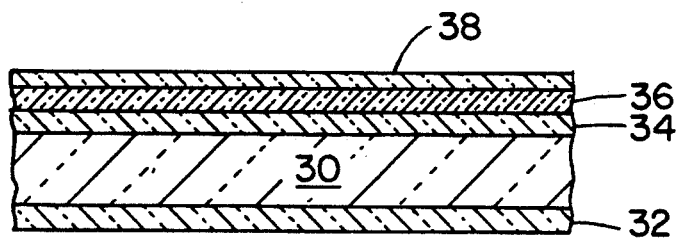
FIGS. 2A–2L is a preferred process flow sequence illustrating the fabrication of a circuit panel for a flat panel display.
Figure 2B:
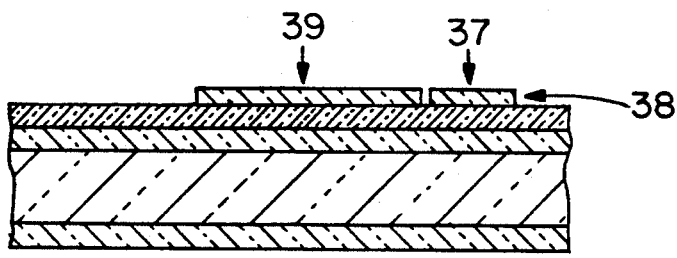
Figure 2C:
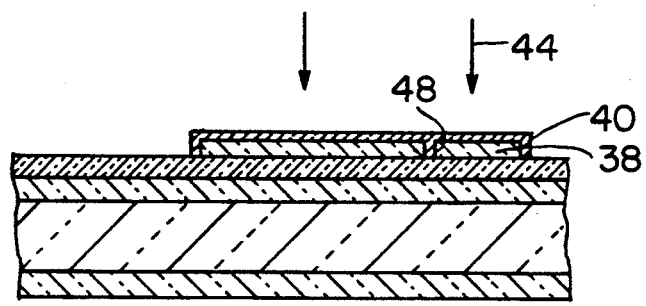

As shown in FIG. 2B, the film 38 is patterned to define a transistor region 37 and a pixel electrode region 39 for each pixel. An oxide layer 40 is then formed over the patterned regions including channel 48 between the two regions 37, 39 of each pixel. The intrinsic crystallized material 38 is than implanted 44 (at FIG. 2C) with boron or other p-type dopant to provide a n-channel device (or alternatively, an n-type dopant for an p-channel device).

Figure 2D:
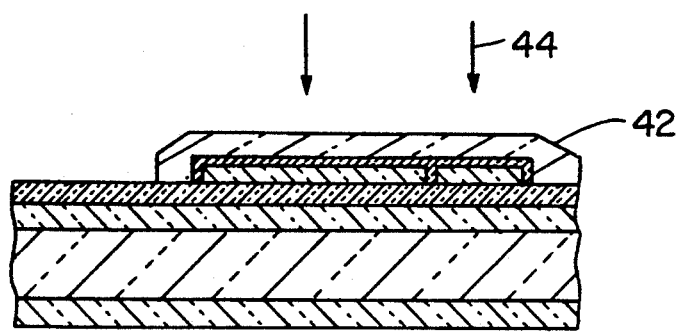
Figure 2E:
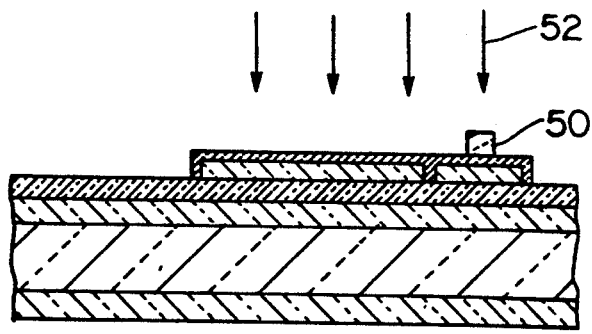
Figure 2F:
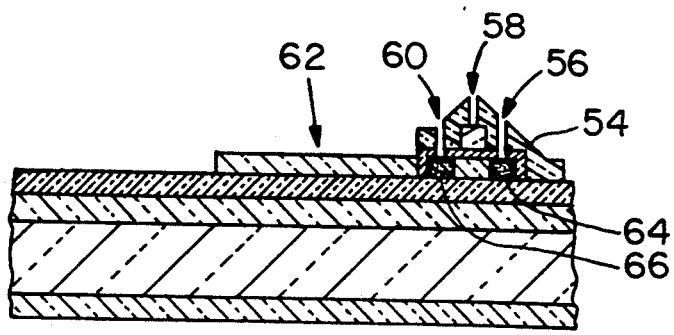
Figure 2G:
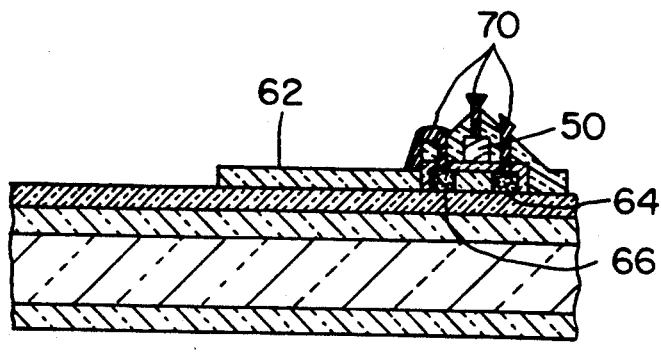
Figure 2H:
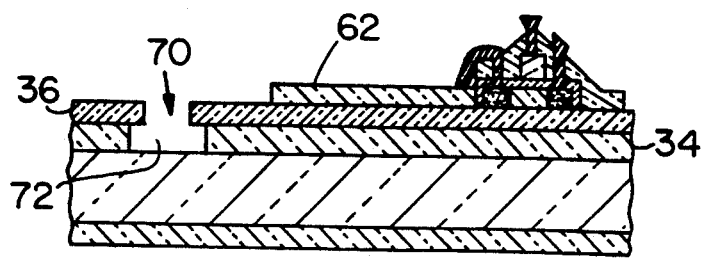

A polycrystalline silicon layer 42 is than deposited over the pixel and the layer 42 is then implanted 46, as seen in FIG. 2D, with an n-type dopant to lower the resistivity of the layer 42 to be used as a gate. The polysilicon is patterned to form the gate 50, as seen in FIG. 2E, which is followed by a large implant 52 of boron to provide p+source and drain regions for the transistor. As shown in FIG. 2F, an oxide 54 is formed over the transistor and openings 60, 56, 58 are formed through the oxide 54 to contact the source 66, the drain 64, and the gate, respectively. A patterned metalization 70 of aluminum, tungsten or other suitable metal is used to connect the exposed pixel electrode 62 to the source 60 (or drain), and to connect the gate and drain to other circuit panel components.

A second fabrication procedure is one of the substrate release processes that have been developed to form thin (1 to 5 micron) films of processed silicon bonded to glass; these films contain active semiconductor devices such as FETs that are partially of completely fabricated prior to transfer. The crystallization and release procedures including the cleavage of laterally grown epitaxial films for transfer (CLEFT) approach are described more fully in U.S. Pat. No. 4,727,047 incorporated herein by reference. The chemical epitaxial lift-off (CEL) approach is described more fully in U.S. Pat. Nos. 4,846,931 and 4,883,561. Both of the CLEFT and CEL techniques permit the reuse of the substrate, leading to reduced cost compared to other approaches in which the substrates are consumed. By combining thin film release techniques with SOI wafers, we will be able to form the required high quality films and circuits on glass.

The foregoing indicates that CEL processes can be limited by the lateral distance that is required for the HF (or other etchant) undercut of the release layer. The key to large area panels using CEL is the release of patterned devices and/or circuits rather than complete large-area films, because the circuits or devices have unused areas that can be used as vertical channels through the film to allow the etch to reach the release layer. This approach is illustrated in FIGS. 2H–2L. To remove the circuit from the release substrate a first opening 70 (in FIG. 2H) is formed in an exposed region of layer 36 that occurs between pixels. A second larger portion of layer 34 is than removed to form cavity 72 such that a portion of layer 36 extends over the cavity 72.

Figure 2I:
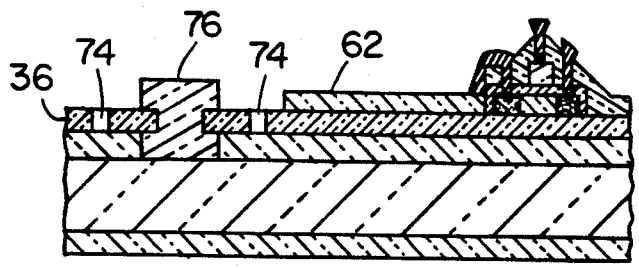
Figure 2J:
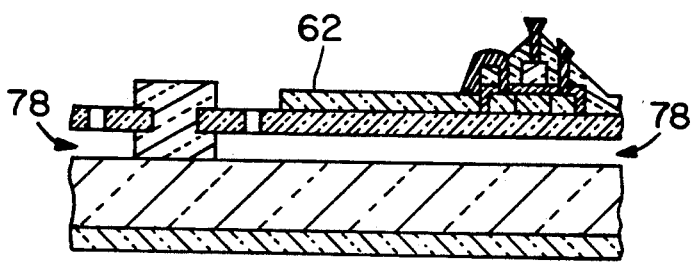
Figure 2K:
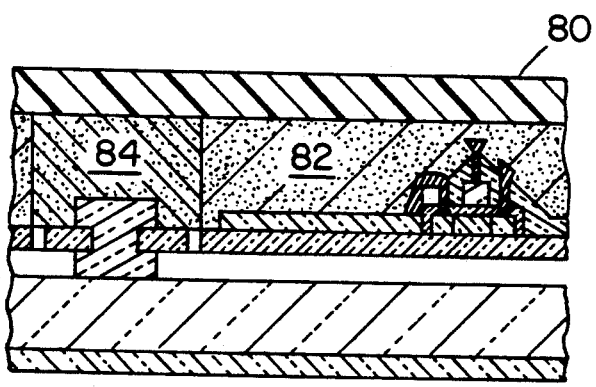

In FIG. 2I, a support post 76 is formed to fill cavity 72 and opening 70, and which extends over a portion of layer 36. Openings or via holes 74 are then provided through layer 36 such that an etchant can be introduced through holes 74, or lateral openings 78, to remove layer 34 (see FIG. 2J). The remaining insulating layer 36 and the circuitry supported thereon is now held in place relative to substrate 30 with support posts 76.

An epoxy that can be cured with ultraviolet light is used to attach an optically transmissive substrate 80 to the circuitry, and layer 36. The substrate 80 is than patterned such that regions of epoxy 84 about the posts 76 remain uncured while the remaining epoxy 82 is cured (see FIG. 2K). The substrate 30 and posts 76 are removed to provide the structure shown in FIG. 2L, which is than processed to provide the desired display panel.

Note that the UV-cured adhesive (or tape) can be patterned to protect the circuits where necessary, and HF can be used to reach the remaining the release layer.

Note that where tape is used, tape provides support to the circuits after release. Large area GaAs devices containing films have been fabricated in this way, and these have been released to form devices from entire wafers on one tape. The released circuits can be remounted on the glass and the other elements of the liquid crystal display panel. Transparent adhesives are the preferred method of mounting.

Figure 2L:
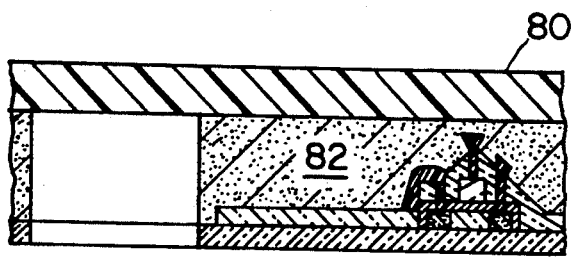

To form the final display panel the circuit panel shown in FIG. 2L is etched leaving the desired pixel elements exposed. Insulation and alignment layers, spacers, a sealing border and bonding pads for connections as added onto the circuit panel. A screen printing process can be used to prepare the border. The plate containing the color filters and the counterelectrode is sealed to the circuit panel with the sealing border after insertion of spacers. The display is filled with the selected liquid crystal material via a small filling hole or holes extending through the border. This filling hole is then sealed with a resin or epoxy. First and second polarizer films or layers are than bonded to both sides and connectors are added. Finally, a white light source 114, or other suitable light source, is coupled to polarize 112.

Figure 3:
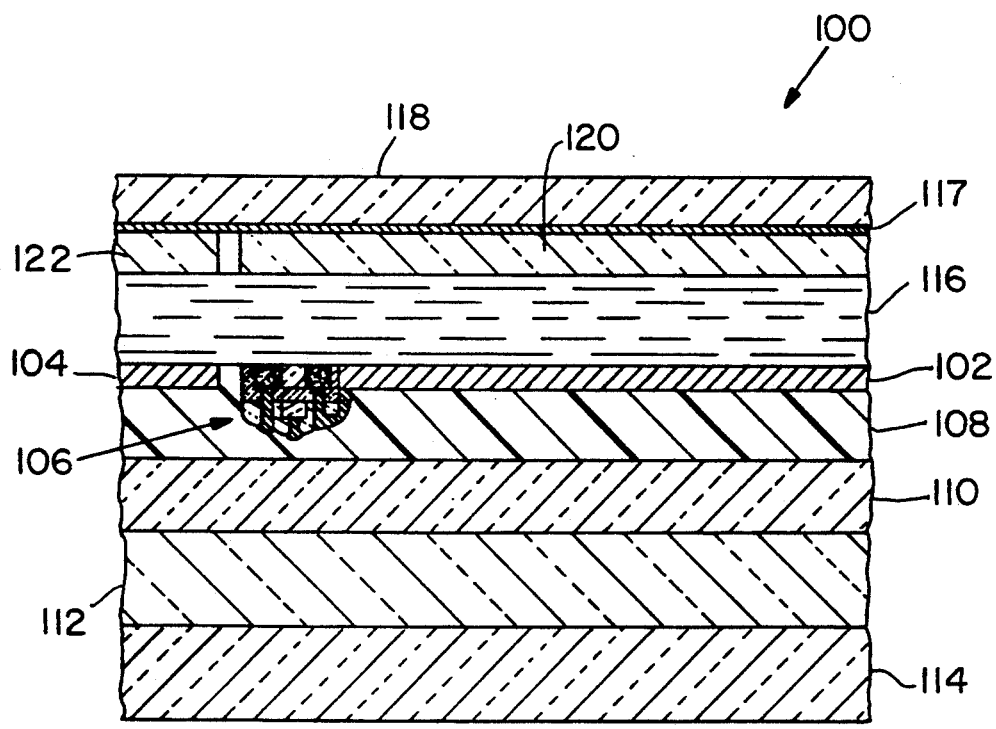
FIG. 3 is a cross-sectional view of a preferred embodiment of the display panel.

A cross-sectional view of the resulting device is shown in FIG. 3 wherein pixel electrodes 102 and 104 are laterally spaced from each other. Each pixel 102, 104 will have a transistor 106 and a color filter 120, 122 associated therewith. Polarizing elements 112, 118 are positioned on opposite sides of the structure which also includes bonding element or adhesive 108 and optically transmissive substrate 110, such as glass or plastic. Layer 108 can be a transparent epoxy or a low temperature glass that can have a thickness of 2–10 microns.

The CLEFT process permits the separation of a thin single-crystal films, grown by chemical vapor deposition (CVD), from a reusable homoepitaxial substrate. Unlike the CEL process, in the CLEFT process the circuits or devices are first bonded to glass and after mounting the separation is made between the circuits and the substrate.

The films removed from the substrate by CLEFT are essentially single-crystal, of low defect density, are only a few microns thick, and consequently the circuit panel has little weight and good transmission characteristics. For the purposes of the present application, the term "essentially single crystal" means a film in which a majority of crystals extend over a cross sectional area in a plane of the film of at least 0.1 cm$^2$, and preferably in the range of 0.5–1.0 cm$^2$ or more.

The CLEFT process, illustrated in U.S. Pat. No. 4,727,047 involves the following steps: growth of the desired thin film over a release layer (a plane of weakness), formation of metallization and other coatings, formation of a bond between the film and a second substrate such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon the lateral epitaxy is accomplished by the ISE process or other recrystallization procedures. Alternatively, other standard deposition techniques can be used to form the necessary thin-film essentially single crystal material.

One of the necessary properties of the material that forms the release layer is the lack of adhesion between the layer and the semiconductor film. Since a weak plane has been created by the release layer, the film can be cleaved from the substrate without any degradation. The release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated resulting in simpler handling as compared to UV-cured tape.

In the ISE process, the oxide film is strongly attached to the substrate and to the top Si film which will contain the circuits. For this reason, it is necessary to reduce the strength of the bond chemically. This technique involves a release layer that is preferentially dissolved with an etchant without complete separation, to form a plane of weakness in the release layer. The films can then be separated mechanically after the glass is bonded to the circuits and electrodes.

Mechanical separation is accomplished as follows: The upper surface of the film is bonded with a transparent epoxy to a superstrate such as glass. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing is completed on the back surface of the film. Note that since the device remains attached to a superstrate, the back side can be subjected to standard wafer processing, including photolithography.

The method further involves the preparation of single crystal films, with seeding in the case of an Si substrate and without seeding for the case of foreign substrates. For the case of seeded Si films, the standard recrystallization process is employed. In either case, the bottom oxide or nitride layer can be optimized for release purposes.

Figure 4:
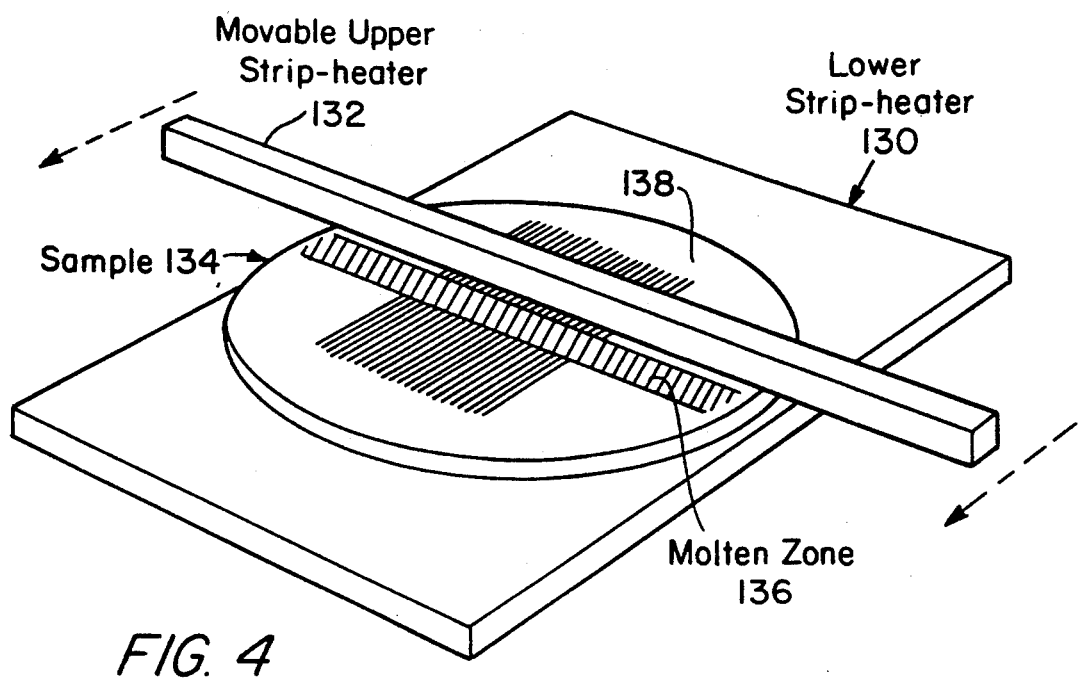
FIG. 4 illustrates in a perspective view a preferred embodiment of a system used for recrystallization.

In one embodiment of the recrystallization system, shown schematically in FIG. 4 the substrate temperature is elevated to near the melting point by a lower heater 130. An upper wire or graphite strip heater 132 is then scanned across the top of the sample 134 to cause a moving melt zone 136 to recrystallize or further crystallize the polycrystalline silicon. In the standard process on Si, the lateral epitaxy is seeded from a small opening through the lower oxide, and the resultant single crystal film has the orientation of the substrate. Capping layer 138 is deposited over the polycrystalline material prior to crystallization.

Figure 5A:
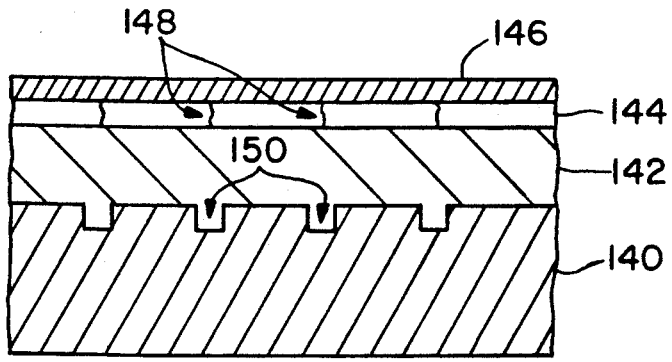
FIG. 5A illustrates the use of a patterned release layer to entrain boundaries in a crystallized material.

The use of foreign substrates precludes seeding. In this case, essentially single crystal Si is obtained by grain boundary entrainment techniques. Grain boundary entrainment can be used by patterning either the release oxide or the cap layer to introduce a modulation in the thermal gradients in the regrowth region. This modulation in the temperature field changes the location of the melt front and entrains the boundaries in predictable locations. Patterning of the release oxide 142 is shown in FIG. 5A. In this embodiment the substrate 140 has grooves 150 which are filled with the release oxide 142. Owing to this entrainment of boundaries 148 in the crystallized material 144 that can extend between the cap 146 and the release layer 142, the Si circuits or electrodes can be located in regions of high quality. Metallization and other features can be located over subgrain boundaries.

As shown, a preferable technique is to pattern the reusable substrate with the necessary entrainment structure. Once patterned in this way, the reusable substrate would not require repatterning. In such a scheme the entraining grooves are provided with a material of sufficient thickness to entirely fill the grooves. The material in the grooves could for example, comprise planarized $Si_3N_4$, while the release layer could comprise further deposition of $SiO_2$. Alternatively, the grooves could be filled entirely with $SiO_2$; the grooves could then function as channels for the release etch.

Figure 5B:
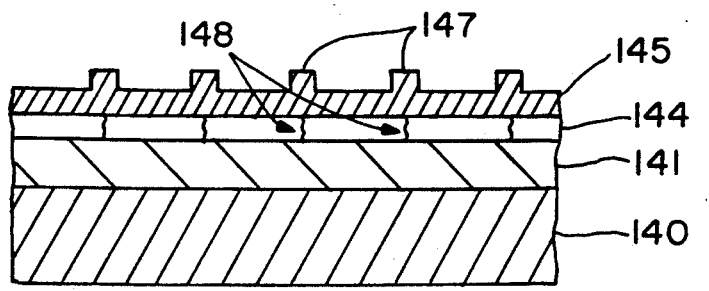
FIG. 5B illustrates the use of a patterned capping layer to entrain boundaries.

A second approach involves patterning the cap layer 145 after cap deposition, as shown in FIG. 5B. Patterned ridges 147 of the cap 145 overlie boundaries 148 in the recrystallized material that can extend between the cap 145 and release layer 141. A third approach would be to pattern the polycrystalline silicon layer.

Capping layers can be used with foreign substrates. The capping layer must be adherent throughout the thermal cycle, but must be removable for device processing. A cap works well for smooth Si substrates, but the patterned layers necessary for entrainment can require new films.

Figure 6A:
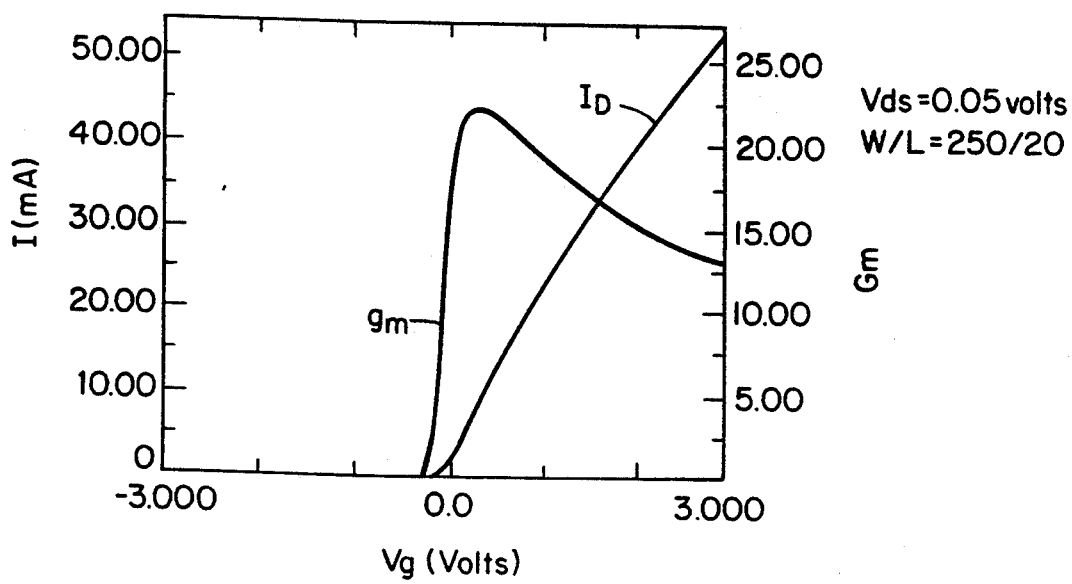
FIG. 6A illustrates the drain current and transconductance characteristics for a MOSFET prior to transfer to glass in accordance with the invention.
Figure 6B:
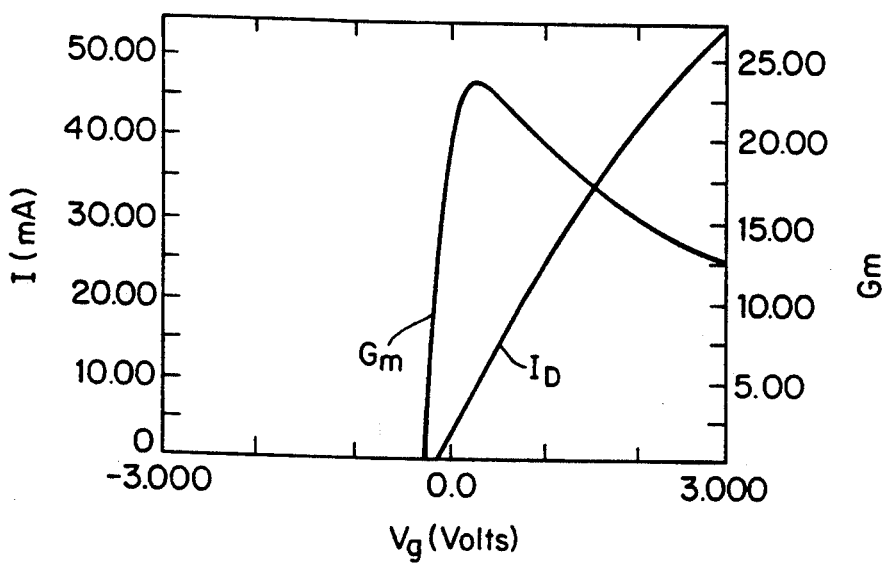
FIG. 6B illustrates the drain current and transconductance characteristics for the MOSFET of FIG. 6A after transfer to glass.

FIGS. 6-8 illustrate the electrical characteristics of a MOSFET made in accordance with the invention before and after transfer onto a glass substrate. FIG. 6A graphically depicts the drain current $I_D$ and the transconductance $G_M$ as a function of gate voltage $V_G$ in the linear region, where the drain-source voltage is 50 mV, for a MOSFET prior to transfer to glass. The MOSFET has a width-to-length ratio of 250 lm/20 lm and a gate oxide thickness of 890 A in a 0.5 lm thick recrystallized silicon material. FIG. 6B shows the drain current $I_D$ and transconductance $G_M$ of the same device after transfer to glass.

Figure 7A:
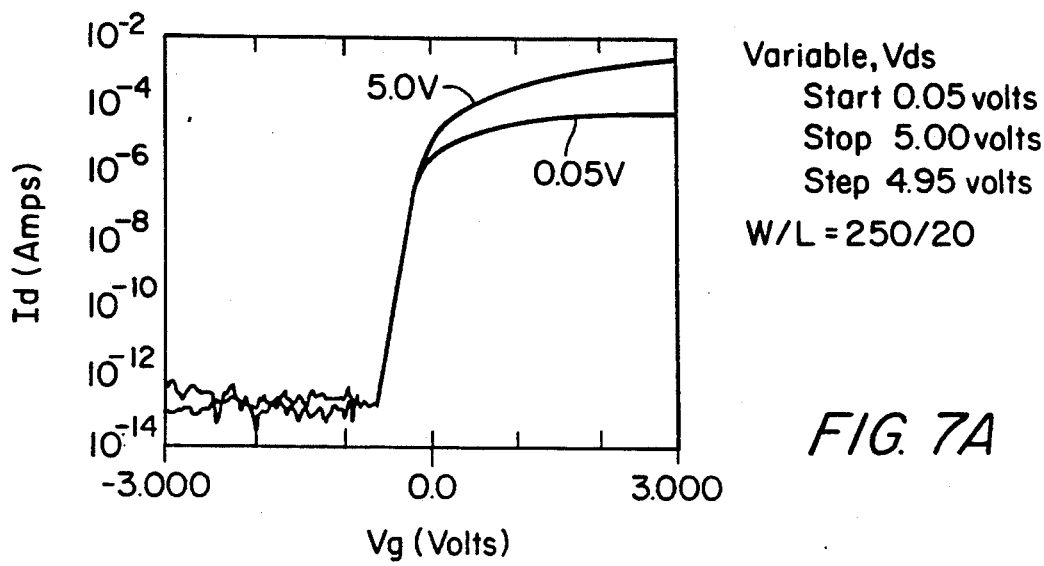
FIG. 7A illustrates the drain current of the device in FIG. 6A plotted on a logarithmic scale at two different drain voltages.

FIG. 7A graphically illustrates the drain current of the device of FIG. 6A plotted on a logarithmic scale at two drain-source voltages $V_{DS}=50$ mV and $V_{DS}=5$ V.

Figure 7B:
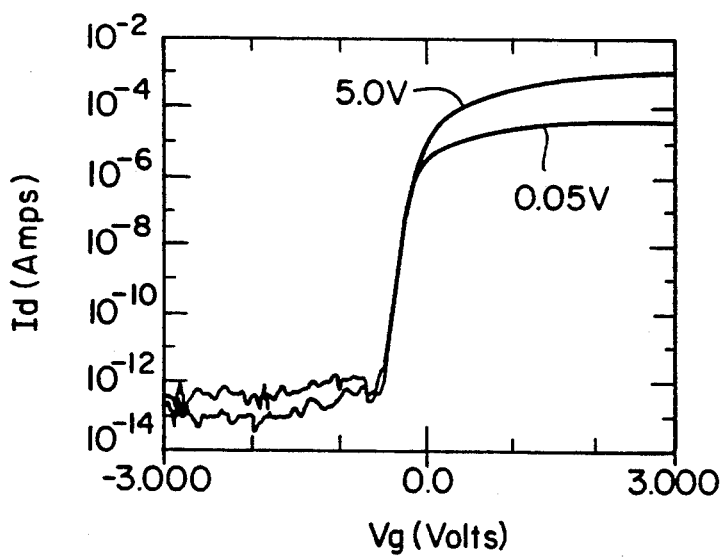
FIG. 7B illustrates the drain current of the device in FIG. 6B plotted on a logarithmic scale at two different drain voltages.

FIG. 7B graphically illustrates the drain current of the device in FIG. 6B poltted on a logarithmic scale at drain-source voltages of $V_{DS}=50$ mV and $V_{DS}=5$ V.

Figure 8A:
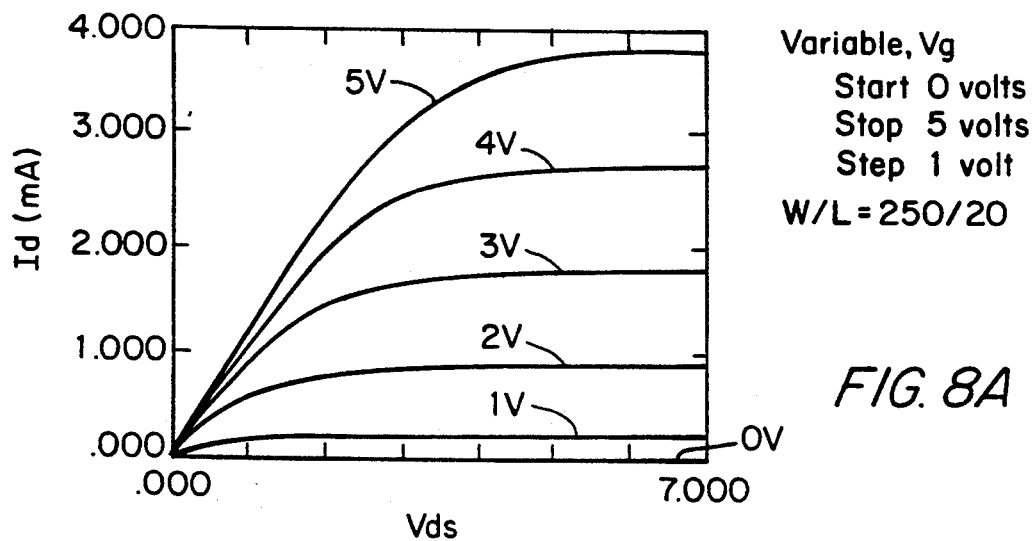
FIG. 8A illustrates the drain current output of the device of FIG. 6A with the gate voltage varying between 0 and 5 volts.

FIG. 8A graphically illustrates the drain current $I_D$ as a function of drain-source voltage of the device of FIG. 6A at gate voltages of $V_{GS}=0, 1, 2, 3, 4$ and 5 volts.

Figure 8B:
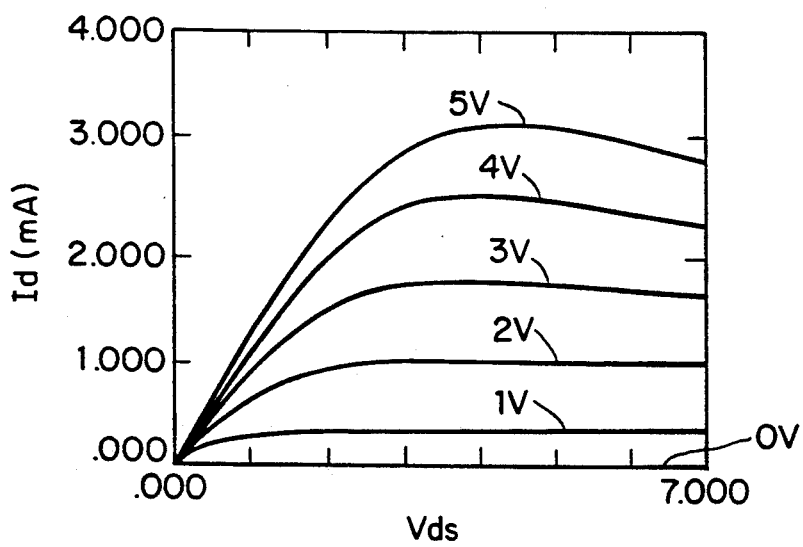
FIG. 8B illustrates the drain current output of the device of FIG. 6B with the gate voltage varying between 0 and 5 volts.

FIG. 8B graphically illustrates the drain current $I_D$ as a function of drain-source voltage of the device of FIG. 6B at gate voltages of $V_{GS}=0, 1, 2, 3, 4$ and 5 volts.

For the CEL approach, a further embodiment involves remounting of the released circuits on glass plates. The application method insures uniform intimate contact between the thin-film semiconductor and the adhesive, yet must not crack or introduce other defects in the thin films.

Methods involve the application of Apiezon W wax to the frontside of the layer to be separated. The stress in the wax imparts a curvature to the lifting layer thereby allowing the etching fluid access to the etching front. Access to the etching front is achieved only from the outer edge of the total area being lifted off.

This process is of limited use for applications involving large area liftoff, however, due to long liftoff times that can extend up to hours or days for areas larger than 2cm×2cm. Curvature is required to increase etchant access to the etching front. However, the curvature necessary for liftoff is caused by a low temperature wax so that no high temperature processing can be done while this wax is present. Present samples are often cleaved to size, not allowing for substrate reuse. The wax application process is automated and patternable to allow for substrate reuse in applications where this procedure is preferred. This process is useful only for individual small areas that do not require backside processing.

Figure 9A:
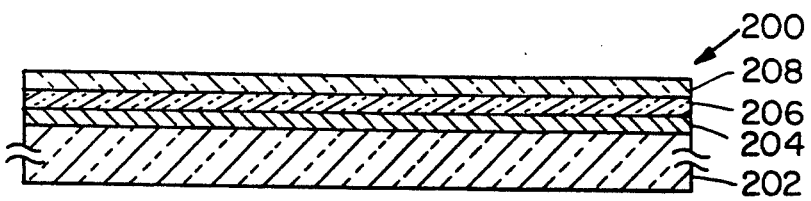
FIGS. 9A–9C are a series of cross-sectional diagrams illustrating a lift-off process in accordance with the invention.
Figure 9B:
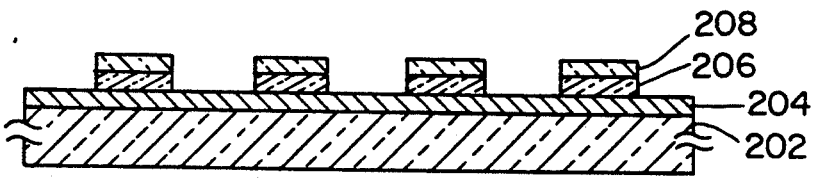
Figure 9C:
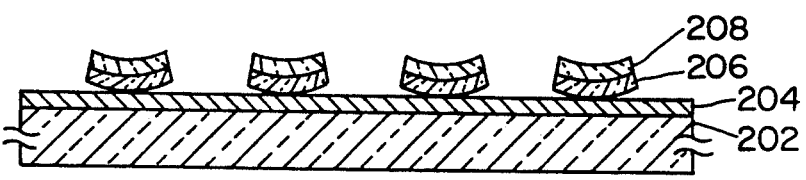

Another embodiment of the invention involves using a combination of thin or thick film materials with different coefficients of expansion to replace the black wax in the standard liftoff process. This process is illustrated in FIGS. 9A–9C. By using the correct temperature the curvature needed for liftoff is achieved due to the differential stresses in the layers. A single layer can be used if it has the correct expansion coefficient with respect to the material being lifted off. This method allows for support layers that impart the correct curvature at the liftoff temperature, lay flat at room temperature, and also support the film during backside processing.

This embodiment of the invention will now be described in connection with structure 200 of FIGS. 9A-9C. A substrate 202, which can comprise any suitable substrate material upon which epitaxial layers or devices can be formed, is provided. A release layer 204 is grown, preferably by CVD, on substrate 202. For a thin-film silicon releasable layer, an $SiO_2$ layer can be used as previously described.

A semiconductor layer structure 206 is formed on release layer 204, also by CVD or other previously described methods. Structure 206 preferably comprises materials arranged for the fabrication of an array of transistors in accordance with the invention.

By using CVD, for example, structure 206 can be made very thin, i.e., less than about 5 microns and, preferably, less than 2 microns, with the contact layer being less than 0.1 micron thick.

The necessary dopants are typically introduced by diffusion or implant after the growth processes to define source, drain and channel regions. Next, the structure 206 is processed on the front, or top side, using conventional techniques to form gates and metal contacts where each pixel is to be located and buss bars and bonding pads, as required.

In a first lift-off embodiment, a coating 208 is then formed on the front side processed structure 206 (FIG. 9A). The coating consists of a combination of thick or thin film materials with different thermal coefficients of expansion. For example, coating 208 can comprise a nitride, metal, bi-metal or a glass stressed coating. Contact metallization (not shown) can also be applied at this time on the contact layer.

The coating layer 208 and structure 206 are then patterned using conventional photolithography and the coating material 208 and structure 206 is removed in predetermined areas down to release layer 204 as shown in FIG. 9B, by etching with a suitable selective etchant. The above steps are performed at a predetermined temperature which is sufficiently low no significant thermal stress between the coating materials of coating 208 is produced. Next, the temperature is elevated to a sufficient degree, causing thermal stress in the coating 208. While at this elevated temperature the structure is exposed to a release etchant (See FIG. 9C).

The release etchant eventually etches the release layer 204 sufficiently to allow separated device structures 206 supported by the coating 208 to be removed. These structures are then brought down to a lower temperature at which the thermal stress is relieved to allow the discrete devices to lay flat for subsequent backside processing.

This process provides a significant advantage over the Gmitter et al. black wax process in that it enables the discrete chips to lay flat for backside processing and the support structure is formed of materials, such as glass, which are impervious to the backside processing temperatures.

Two different procedures can be used to achieve wafer scale liftoff. The first method involves the etching of the entire substrate on which the film to be transferred has been formed. This is termed an "etch back" procedure.

A second method accesses the release layer from the edge of the wafer or sample only and releases the material as one large sheet. This second method is for cases which do not require registration between devices lifted from the same wafer. If registration is not desired, an automated procedure is used for liftoff of large areas of individual devices or areas of material. After frontside processing is completed, UV cured epoxy can be cured with the desired pattern, removed where it is not wanted, and then used as the mask for etching down to the release layer. The UV cured epoxy can then be left on and can act as support for the lifted films after separation. The separate devices would need to be retrieved from the etching solution and processed separately using pick and place type methods.

These alternative lift-off processes will now be described in connection with FIGS. 10A-10E, wherein corresponding items in FIG. 9 retain the same reference numeral if FIG. 10. As shown in the partial perspective cross-section of FIG. 10A, a substrate 202 has formed thereon a release layer 204, followed by a device structure 206, all as described in connection with FIG. 9. All front side processing, such as bonding pads and metal contacts (not shown) to the structure 206 are completed.

A material which can be transformed from a less soluble or less etchable state to a more soluble or more etchable state (or vice versa) is formed on the front-side processed structure 206. For example, a UV curable epoxy 230 can be spread over the structure 206. This epoxy has the property that exposure to UV light causes it to be less soluble.

A UV light transparent mask release layer 232 of material is then formed over the epoxy 230 and a patterned opaque mask 234 with openings 236 is affixed over the layer 232.

The mask 234 is irradiated with UV light, curing the areas of the epoxy underlying the mask openings 236 and making them less soluble than in the uncured state. The release layer 232 is removed by and the mask 234 is removed. Next, the uncured epoxy is removed by a solvent, such as down to the release layer 204 (See FIG. 10B).

The cured epoxy 230 is left on the structure to serve as a support for the thin film structure 206 after separation from the release layer 204. In this manner, the etching front is increased by dividing up the total top surface area of structure 206 into smaller areas by cutting channels 240 down to the release area 204.

A second method for wafer size liftoff relies on increasing the amount of etching front by dividing up the total area to be lifted into smaller areas. Channels are cut into the total area of material to be lifted thereby exposing the release layer. These channels can completely separate the area or can consist of slits cutting part way into the liftoff area.

Figure 10A:
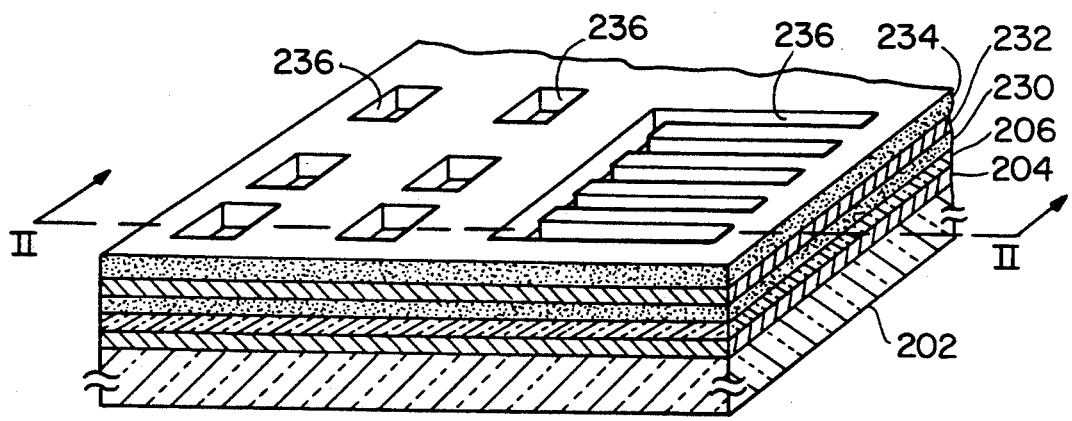
FIG. 10A is a partial perspective view of a wafer during lift-off processing according to another embodiment of the invention.
Figure 10B:
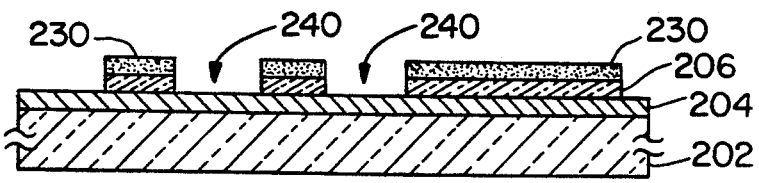
FIG. 10B is a sectional view taken along lines II–II of FIG. 10A of the lift-off structure after a step in the process.
Figure 10C:
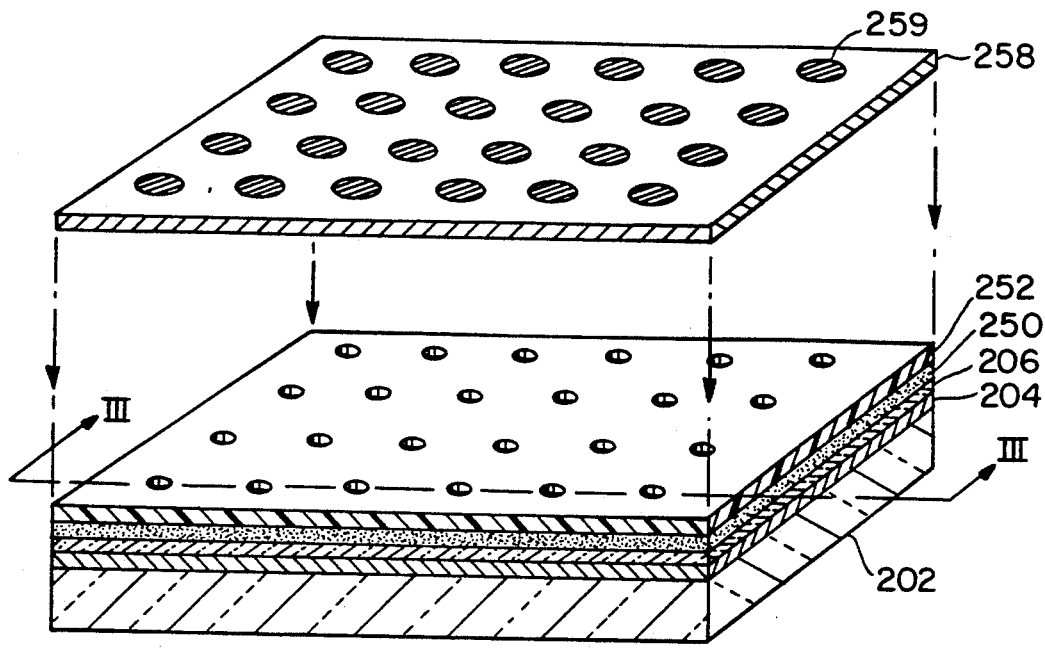
FIG. 10C is a partial perspective view of a portion of a wafer during lift-off processing in another embodiment where registration is maintained.
Figure 10D:
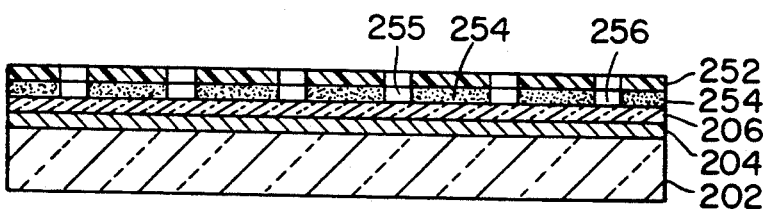
FIGS. 10D and 10E show cross-sections of the structure of FIG. 10C after additional steps in the lift-off process.
Figure 10E:
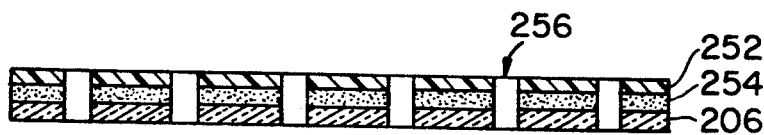

The second method addresses the problem of trying to register these small areas of material with respect to each other while at the same time allowing the etching medium greater access to the exposed release layer. The ability to do this allows for easy retrieval from the solution, wafer scale processing on the backside, and short liftoff times due to the smaller areas and maximum exposure of the etching front. The key feature of this approach is that it allows for registration of the entire wafer area while still providing the etching solution access to all the etching fronts.

Where registration between devices is required, as in an array of transistors, the lift-off method of the alternate embodiment of FIGS. 10C-10E offers many advantages.

This alternate process of FIG. 10C solves the difficult problem of trying to register small device or pixel areas of material with respect to each other, while at the same time, allowing the etching medium access to the exposed release layer. The ability to do this allows for easy retrieval from the solution, wafer scale processing on the backside, and short lift-off times due to the smaller areas and maximum etching front. This approach also enables registration of devices throughout the entire wafer area while still providing the etching solution access to all the etching fronts. Turning to FIG. 10C, there is shown a rectangular partial section of a wafer. The wafer is formed of a semiconductor substrate 202 upon which a release layer 204 is deposited by CVD followed by a front processed transistor panel 206, all as previously described above.

Transformable material, such as uncured liquid UV epoxy 250 is spread onto the top or front surface of structure 206. The point of departure with the previous embodiment occurs in the next step, when a perforated planar grid 252, made of transparent material, such as plastic, is aligned on top of the epoxy 250. The perforations 256 extend orthogonal to, and through, the plane of grid 252.

A photo-mask with opaque circles 256 aligned to cover the perforations 256 is then affixed over the grid 252 (FIG. 10C). (An optional UV transparent mask release layer (not shown) may be formed between the mask 258 and grid 252 to facilitate mask removal.) UV light is focused onto the mask, curing the underlying epoxy 254 everywhere except beneath the opaque circles 254, as shown in FIG. 10D wherein the cured sections of epoxy 250 are shown in shaded section and the uncured sections are in blank. The mask 258 is removed. The uncured epoxy 250 is removed from the openings 256 by a suitable solvent and structure 206 etched away through the openings down the the release layer 204. The release layer is then etched away using the opening 256, as provided above. Access for the etchant is thus achieved at many points across the wafer, resulting in an array being attached to grid 252 by cured epoxy 254 (See FIG. 10E).

Figure 11A:
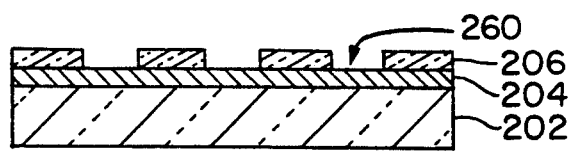
FIGS. 11A–11E are schematic drawings of a wafer during various steps in the process flow of a lift-off procedure in accordance with the invention.
Figure 11B:
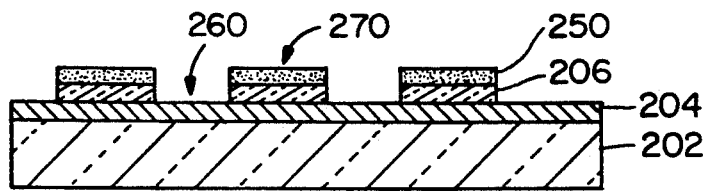
Figure 11C:
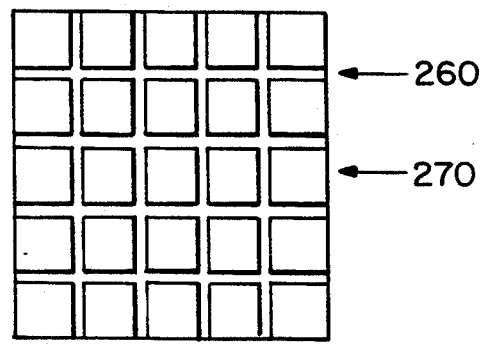
Figure 11D:
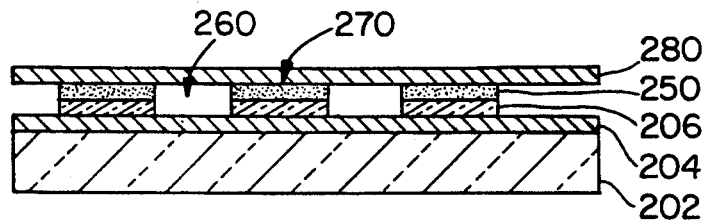
Figure 11E:
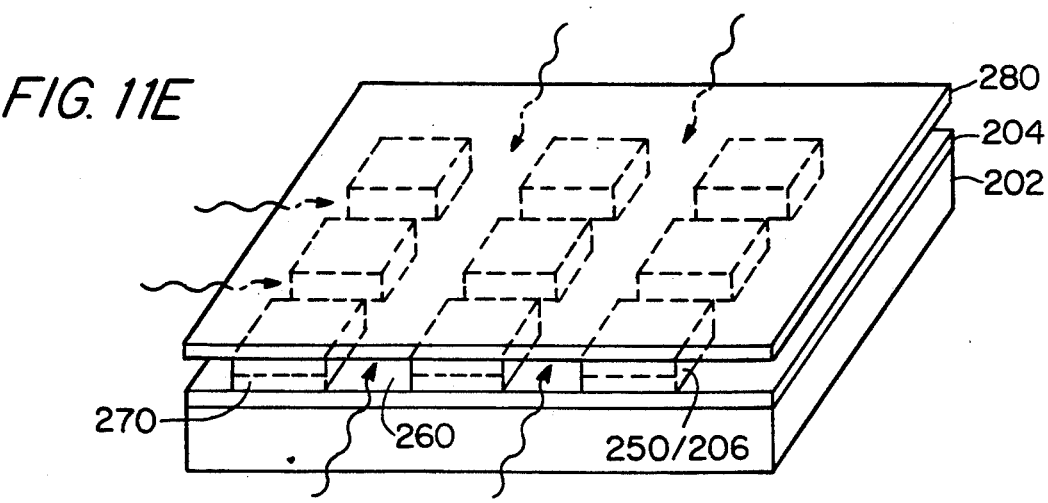

Another approach to registration is to form channels 260 directly in the device material by etching down to the release layer 204, thereby forming channels in the material alone (FIG. 11A). These channels can also be made taller by using the UV cured epoxy patterning method of FIG. 9 and then etching down to the release layer 204, (See FIG. 11B), or any other method that forms channels 260 or access streets between the areas 270 to be separated, as shown in the plan view of FIG. 11C. A support 280 can then be attached to the material 270 over the channels 260 and then the etchant can be allowed to run along the channels, thereby giving the etchant access to the center of the wafers (FIGS. 11D-11E). Taller channels can assist in speeding up the capillary action to achieve faster release. Other methods can also be used to speed along the movement of the etchant up the channels 260, including vacuum assistance, ultrasonic assistance, etc.

Along the same lines, channels 260 can be made in the device material to expose the release layer below. A porous material is then spun on, or otherwise formed or attached to the front surface. This material is rigid or semi-rigid when cured by UV, heat, or solvent treatment, etc., and therefore able to support the lifted film after separation from the substrate. The material is sufficiently porous to pass the etchant fluid without being attacked by the etchant. In this way, the etchant passes through the porous material and is given access to the release layer at its exposed points.

In another embodiment, the release layer etchant is brought in contact with the release layer before the overlying support structure is attached to the structure 206. For this process to work, channels 260 must be formed between devices or areas of material to be lifted for the etchant to be trapped in. The basic process is as follows: Channels 260 are formed between lift-off areas 206 which expose the release layer 204 on substrate 202. This can be done with any of the previously described methods which create channels between devices. A simple method which works very well is to form the channels directly in the material 206 by photoresist masking followed by etching down to the release layer 204. This forms channels 260 in the material which are equal to the height of the material above the release layer. Next, an etchant is placed on the surface of the layer to be lifted, or the wafer is submerged in the etchant. In either case, the channels 260 between the areas to be lifted 206 are filled with the etchant material. After this is done, the overlying support layer, which will also hold the registration after lift-off, is affixed to the front surface of the structure 206 by bonding methods described in detail herein. The overlying support is secured to the material 206 while the wafer is submerged or while the etchant is covering the front surface of the wafer and filling the channels. The support materials must be rigid enough that they do not fill in the channels that have been formed and thereby force the etchant out. A suitable support material can comprise glass, plastic or other optically transmitting substrate. This allows for a solid support medium that does not need etchant access holes in it, thus greatly simplifying the process.

The trapped etchant sufficiently dissolves the release layer 204 so that the thin film area 206 can be removed while being supported and registered by support with the backside exposed for further processing, i.e., formation of backside conductor metallization and bonding pads.

In addition to the support materials referenced above, UV release tapes, which are well known in the industry for handling small devices, have proven to be an excellent support choice for several reasons. These tapes have the property that when exposed to intense UV radiation, they lose most of their adhesion. In addition, moisture does not seem to effect the adhesive, and they can be applied with great success, even if submerged in liquid. These tapes can be used alone or in conjunction with a thicker support. This additional support should be formed of material which is transparent to UV radiation unless it is to be permanent and it should not be attacked by the etchant being used.

Figure 12A:
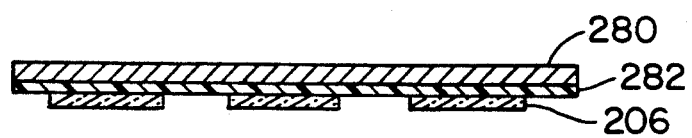
FIGS. 12A–12C are schematic sectional drawings of another preferred lift-off procedure of the invention.
Figure 12B:
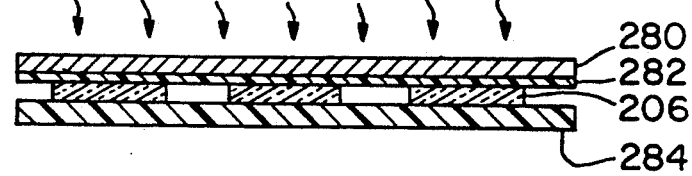
Figure 12C:
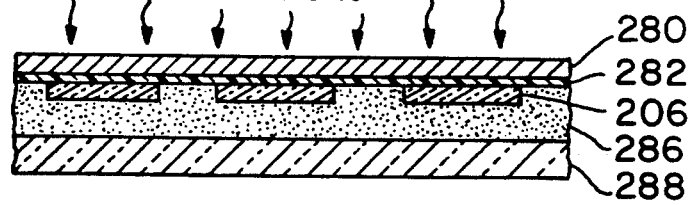

The UV release adhesive can be applied directly to other support materials, instead of the tape backing material. As shown in FIGS. 12A-12C, support 280, combined with double-sided UV release tape 282, can be used. One side of the tape 282 is adhered to the support. Then the other side is adhered to the front of the structure 206 after the etchant is applied. The etchant is then allowed to undercut the device 206. The devices are then attached by release tape to the support 280, as shown in FIG. 12A. The lift-off time is very short because the etchant has access to the release layer from many points on the wafer surface.

In this way, the devices are registered with respect to each other and are supported by the support 280 during backside processing.

The tape's adhesion can then be released by UV irradiation through the support (FIGS. 12B or 12C) and the tape can be taken off the carrier 280 with the devices still attached. Further UV exposure will decrease the adhesion of the devices to the tape to a sufficient degree to allow the devices to be removed by vacuum wand or to be transferred directly from the tape to any other tape 284 or epoxy 286 with substrate 288 (See FIGS.

12B or 12C) or other medium. Separate areas as large as 0.5 cm in width have been lifted by this non-curvature method. Total wafer size, which can be lifted and registered simultaneously, is only limited by the wafer size.

As indicated, an alternative embodiment involves use of UV-cured adhesive tapes and epoxies. The adhesive can be used to bond the thin-film transistors and CMOS circuit elements to glass. The adhesive is applied to plates that are as large, or larger than, 14"×14". Application methods include: spin coating, vapor coating, spraying, and standard thick film application processes to provide the necessary uniformity and optical quality.

Another preferred embodiment includes a method to transfer tightly placed devices to positions not so tightly spaced on the circuit panel. The technique illustrated in FIGS. 13A, B and C uses stretching or contracting of a stretchable tape or film until the devices are positioned correctly. This technique can also include previously described lift-off procedures and mechanical or a combination of stretching and mechanical methods. Commercially available devices can be used to precisely control the stretching of the film. Various methods can be used to measure the spacing of devices during stretching and transfer to provide proper registration of components.

Figure 13A:
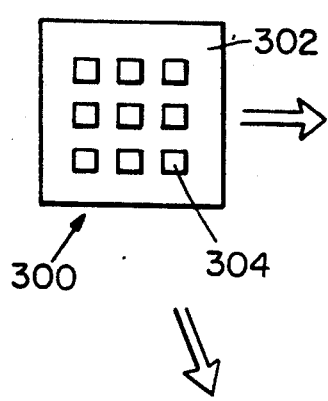
FIGS. 13A–13C schemztically illustrate a preferred method of transfer in accordance with the invention.

As illustrated in FIG. 13A in connection with structure 300, an array of transistors or thin-film semiconductor regions 304 has been transferred onto a stretchable substrate 302. Transistors or regions 304 have been fabricated and trasferred in accordance with the procedures set forth above, or using any other suitable procedure. Substrate 302 can comprise an adhesive.

Figure 13B:
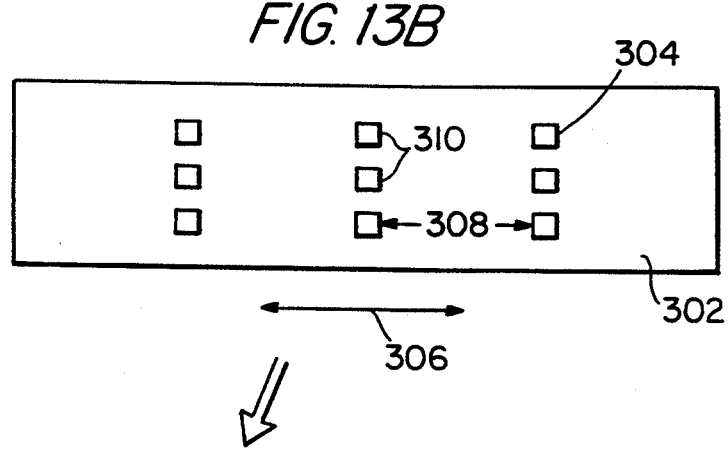

In a first embodiment the structure is stretched along axis 306, as shown in FIG. 13B, thereby increasing the distance 308 between devices 304 along axis 306 while leaving the distance 310 between devices in another direction the same. The substrate 302 is then stretched along axis 314 to produce the array shown in FIG. 13C where devices 304 have spacing 308 in one direction and spacing 312 in an orthogonal direction.

Figure 13C:
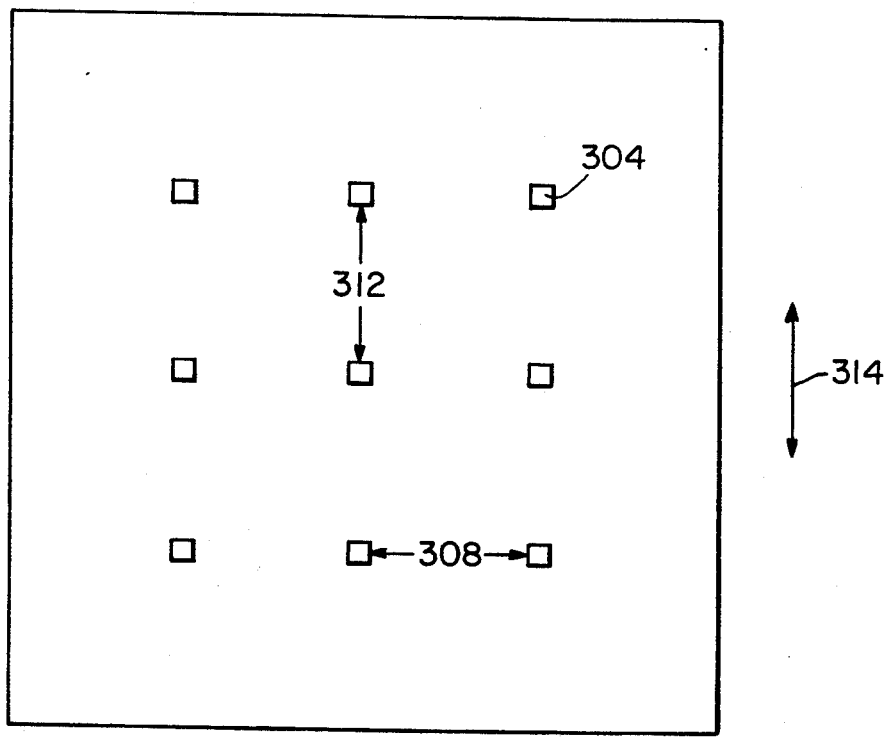

In another embodiment the structures 300 of FIG. 13A is stretched simultaneously in directions 306 and 314 to provide the array shown in FIG. 13C.

Figure 14A:
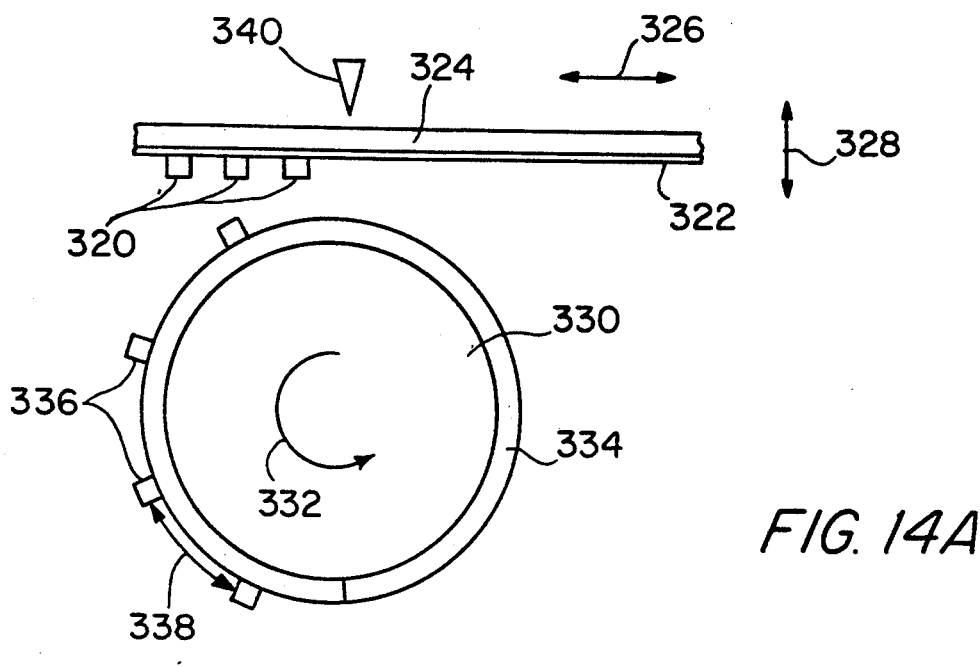
FIGS. 14A and 14B schematically illustrate additional transfer methods in accordance with the invention.
Figure 14B:
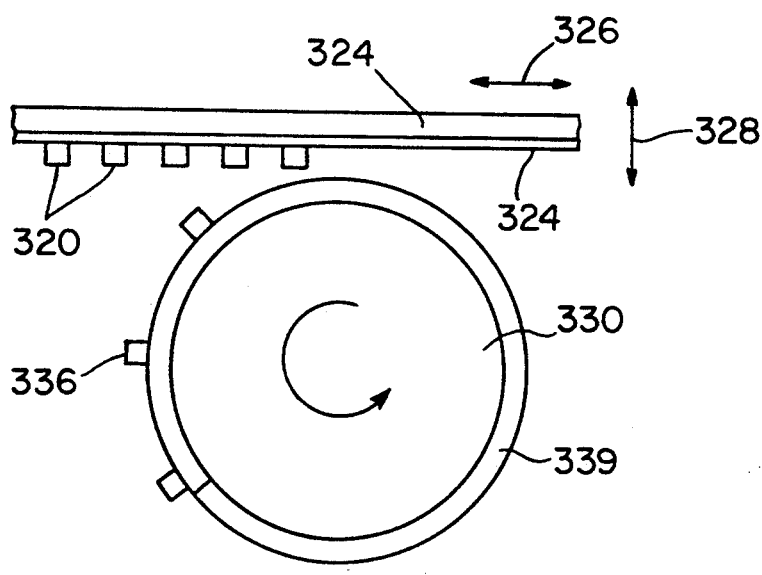

A mechanical technique is shown in FIGS. 14A and B. One starts with a lifted off array of devices 320 on a tape. This tape 322 is placed on a frame 324 that moves in and out along axis 326 and up and down along axis 328. A drum 330 with a flexible tape 334 is placed around its circumference. A instrument 340 is then pushed onto the device 324, pushing the first row of devices onto the drum tape 334. The drum tape 334 is indexed in direction 332 at the necessary angle and again the instrument 340 pushes a second row of devices with spacing 338 onto the tape 334. This continues until all the rows are transferred. This first drum tape 334 with the rows of devices 336 is then put onto frame 324. The same operation continues by transferring rows onto a new drum tape 339.

Another embodiment is to stretch the tape in one direction, transfer this to another tape and stretch that tape in the other direction and transfer the devices to the final support. This method is well suited for small disconnected devices.

Figure 15:
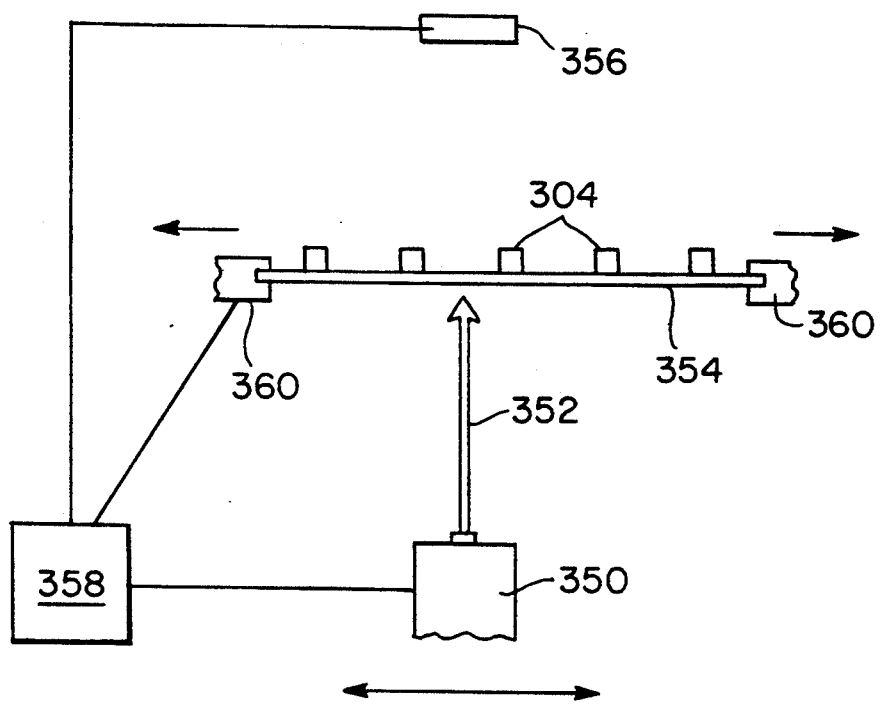
FIG. 15 illustrates a preferred system for monitoring and controlling device registration in accordance with the invention.

A system for measuring the distance between devices 304 on a transfer or final substrate is shown schematically in FIG. 15. A laser 350 directs a beam 352 in the direction of substrate 354 and scans across the source. Sensors 356 are positioned to detect transmitted and/or reflected light an generate signals where the beam is deflected by a device 304. A controller 358 correlates movement of the beam 352 relative to the substrate 354 so that the distance between the devices 304 is accurately measured. Controller 358 is electrically connected to stretching mechanism 360 so that adjustments can be made to the spacing of selected rows or columns of devices.

Stretching mechanism 360 can consist of a piston that is pressed through a collar to which the substrate 354 is attached. The movement of the piston face against substrate 354 and through the collar stretches substrate 354 in a precisely defined manner to increase the spacing between devices 304.

Alternatively, there are commercially available stretching mechanisms like that shown in FIG. 15 which grip the substrate along its periphery and precisely pull the substrate in the appropriate direction.

After stretching the registered devices are transferred to glass, polyester or other suitable substrate for light valve (LCD) fabrication. Alternatively, the devices can be mounted onto light emitting devices for display fabrication.

Figure 16A:
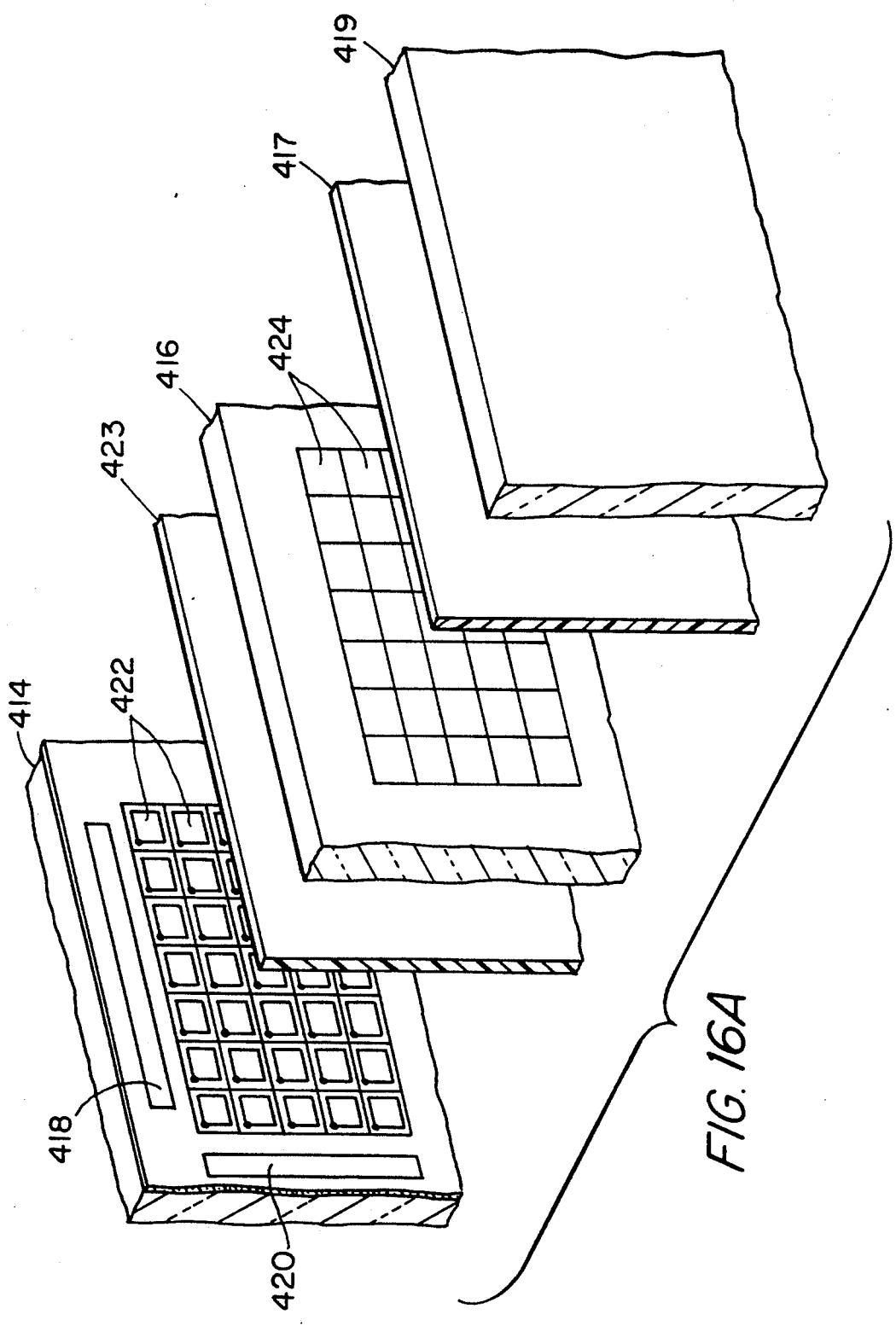
FIG. 16A is an exploded perspective view of an electroluminescent panel display in accordance with the present invention.

As stated previously, other preferred embodiments employ an emissive material such as an electroluminescent film, light emitting diodes, porous silicon or any light emitting material to form each pixel element of the display. To that end, another preferred embodiment of the present invention is illustrated in the perspective view of an electroluminescent (EL) panel display in FIG. 16A. The basic components of the EL display include an active matrix circuit panel 414, a bottom insulator 423, an electroluminescent structure 416, a top insulator 417 and an optically transparent electrode 419, which are secured in a layered structure. The EL structure 416 is positioned between the two planar insulating layers 417 and 423 which prevent destructive electrical breakdown by capacitively limiting direct current flow through the EL structure and also serve to enhance reliability. The insulators 417 and 423 have high electrical breakdown so that they can remain useful at high fields which are required to create hot electrons in the EL phosphor layers. The capacitive structure of the display is completed by producing thin-film electrodes adjacent to each insulator. One of these electrodes is formed within the pixel array 422 and the other electrode is the optically transparent electrode 419 which allows light to exit the display.

The array of pixels 422 formed on the circuit panel 414 are individually actuated by a drive circuit. The circuit has first 418 and second 420 circuit components that are positioned adjacent to the array such that each pixel 422 can produce an electric field in the electroluminescent structure 416 between the pixel electrode and an element of the electrode 419. The electric field causes an EL element 424 to be illuminated.

Figure 16B:
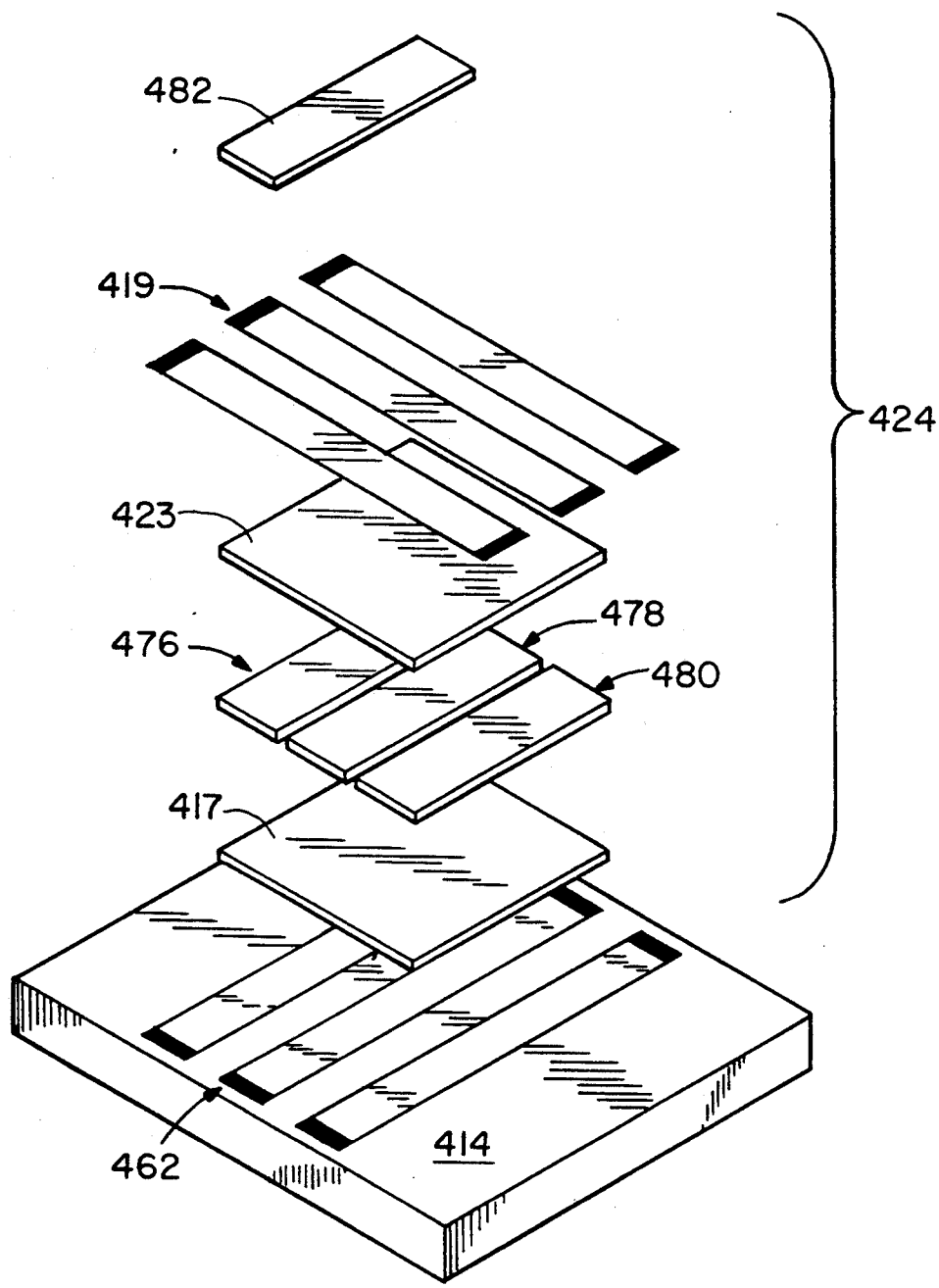
FIG. 16B is a perspective view of an electroluminescent color display element.

The electroluminescent structure 416 may be formed of a single phosphor layer for a preferred embodiment having a monochrome EL display. In another preferred embodiment, the EL structure 416 is formed of a plurality of patterned phosphor layers for providing color display. The phosphor layers are patterned such that each color pixel includes red, green and blue phosphor elements. The EL color display can be formed based on the EL display formation process disclosed in international application PCT/US88/01680 to Barrow et al. incorporated herein by reference. Referring to FIG. 16B, each EL element 424 is divided into single color elements such as red 476 and 482, green 478 and blue 480.

To illuminate a single color element for a given EL element 424, the drive circuit causes an electric field to be formed between one of the bottom electrodes 462 and the transparent electrode 419. For a selected illuminated single color element, the light emitting centers of the phosphor are impact excited by the flow of hot electrons through the phosphor layer when the electric field exceeds a known threshold. As such, the pixels 422 can be selectively actuated to provide any illuminated color for that pixel group.

The active matrix pixel array employs transistors (TFTs) colocated with each pixel in the display to control the function of the pixel. As applied to EL displays, the active matrix approach offers significant advantages including reduced power dissipation in the circuit panel and increased frequency at which the AC resonant driver can operate. The formation of a useful EL active matrix requires TFTs that can operate at high voltages and high speeds. Single crystal silicon is preferred for achieving high resolution in a small (6in×6in or less) active matrix EL display.

In an EL display, one or more pixels are energized by alternating current (AC) which is provided to each pixel by row and column interconnects connected to the drive circuitry. The efficient conduction of AC by the interconnects is limited by parasitic capacitance. The use of an active matrix, however, provides a large reduction of the interconnect capacitance and can enable the use of high frequency AC to obtain more efficient electroluminescence in the pixel phosphor and increased brightness. In accordance with the present invention, the TFTs that provide this advantage are formed in a single crystal wafer, such as bulk Si wafers, or thin-films of single crystal or essentially single crystal silicon. These high quality TFTs are employed in an EL panel display, providing high speed and low leakage as well as supporting the high voltage levels needed for electroluminescence.

In preferred embodiments, single crystal silicon formed on an insulator (SOI) is processed to permit the formation of high voltage circuitry necessary to drive the EL display. More specifically, thin-film single crystal silicon formed by the ISE process or other SOI processes allows for fabrication of high voltage DMOS circuitry for the TFTs as well as low voltage CMOS circuitry for the drivers and other logic elements.

Figure 16C:
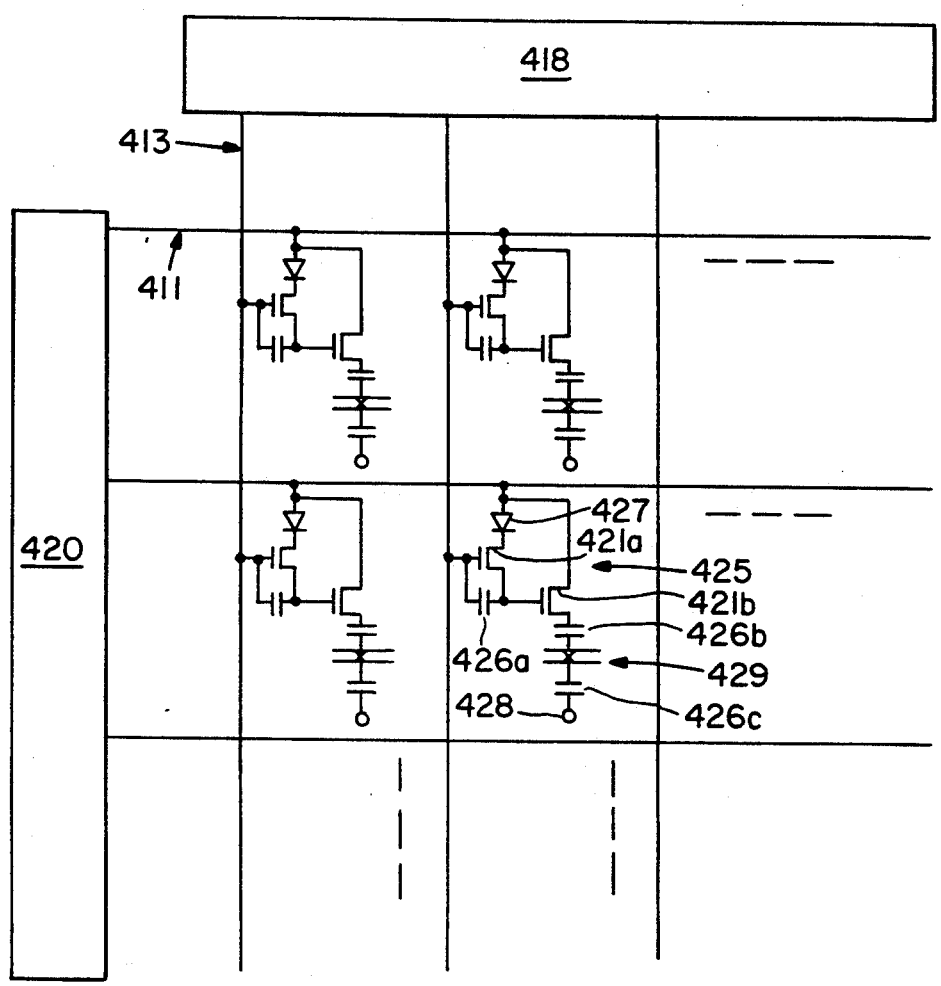
FIG. 16C is a circuit diagram illustrating the driver system for the electroluminescent panel display.
Figure 16D:
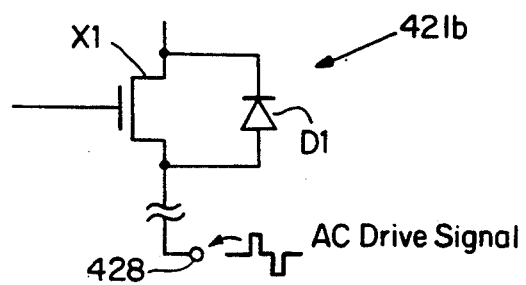
FIG. 16D is an equivalent circuit for a DMOS transistor of FIG. 16C.

The DMOS/CMOS drive circuitry configuration for controlling an EL monochrome display is illustrated in FIGS. 16C–16D. Each active matrix EL pixel circuit 425 includes a CMOS and DMOS transistor (TFTs) 421a and 421b respectively. The capacitors 426a, 426b and 426c represent the parasitic and blocking capacitors normally present in an AC EL structure. Despite its complicated appearance, each pixel circuit 425 should actually occupy only a small fraction of the pixel area even with array densities of up to 1000 lines/inch. The drive circuitry for an EL monochrome display is shown for simplicity purposes only. For an EL color display, the drive circuitry for each pixel would comprise three pixel circuits 425 selectively activated to drive the red, green or blue color elements.

Referring to FIG. 16C, there are two unique aspects of the pixel circuit 425. The first is that the use of the DMOS transistor 421b on the output of the drive circuit allows the EL display to be driven with an AC drive signal at 428. This feature can be appreciated by considering just the DMOS transistor.

Referring to FIG. 16D, an equivalent circuit for a DMOS transistor 421b includes an NMOS device X1 with a shunting diode D1. If the gate on the NMOS transistor X1 is raised to the threshold voltage above the source, current will flow through the transistor X1 during the positive AC drive pulse. The presence of the shunt diode D1 allows current to flow in the reverse direction regardless of the gate voltage, so that with a high gate voltage, current flows through the transistor X1 during both the positive and negative transitions. The EL layer 429 is therefore being excited and will be illuminated as long as the gate is held high. If the gate is held low, that is at a voltage below the threshold voltage $V_t$, then the transistor X1 will not conduct during the positive drive pulse. Thus, the EL layer 429 will only see a series of negative pulse and will charge to the pulse potential during the first negative pulses and be prevented from discharging during the positive pulse by the rectifying behavior of the diode D1. Therefore, after a single brief illumination period, the EL layer 429 will remain passive since the total voltage across it and its isolation capacitors 426b and 426c remains constant.

Referring back to FIG. 16C, the second unique feature of the circuit 425 is that it can be controlled by only two wires. The second feature is achieved in the present invention through the use of a p-channel MOS transistor 421a, and a diode 427. The diode 427 may be fabricated as a lateral or vertical structure and would not add significantly to the overall area or complexity. The diode 427 is needed because the NMOS transistor 421a is a symmetric device and would otherwise discharge the capacitor 426a during the illuminate period rendering the circuit and display inoperable.

To insure the performance of the circuit 425, a circuit analysis was performed. The circuit 425 operates by first charging the capacitors 426a by applying a low signal to the select line 413 (0 volts) in the analysis and then raising the data line 411 to the desired voltage (in a range from 0.5 to 2 volts in this analysis). After the charging sequence, the capacitor 426a will be charged to a voltage approximately equal to the difference between the data and select line signal levels and minus the diode 427 forward voltage drop. To turn on the output transistor 421b, the select line 413 is first increased to about 1 volt and the data line 411 is ramped from −2 volts to 0 volts. The output transistor 421b remains on for a time which is directly proportional to the voltage that was stored on the capacitor 426a. In this way, grey scale is achieved by the circuit 425.

A preferred EL display formation process includes the formation of a single crystal silicon film, fabrication of active matrix circuitry on the silicon film and integration of EL materials to form the emissive elements. To that end, FIGS. 17A–17K illustrate the Isolated Silicon Epitaxy (ISE) process to form a silicon-on-insulator (SOI) film as well as a process for fabricating high voltage DMOS devices and low voltage CMOS devices on the ISE film to form circuit panel circuitry. Note that while the ISE process is shown herein, any number of techniques can be employed to provide a thin-film of single crystal Si.

Figure 17A:
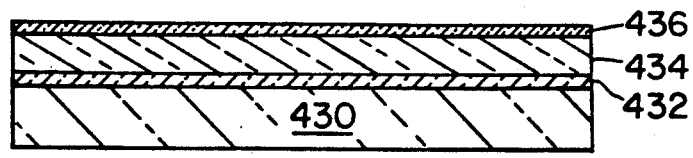

An SOI structure, such as that shown in FIG. 17A, includes a substrate 430 and an oxide 432 (such as, for example $SiO_2$) that is grown or deposited on the substrate 430. A polycrystalline silicon film is deposited on the oxide 432, and the poly-Si film is capped with a capping layer 436 (such as for example, SiO$_2$). The structure is the heated near melting point, and a thin movable strip heater (FIG. 4) is scanned above the top surface of the wafer. The heater melts and recrystallizes the silicon film that is trapped between the oxide layers, resulting in a full area single crystal silicon film 434.

A thin single crystal layer of silicon 434 is thus formed over the oxide 432 such that the oxide (or insulator) is buried beneath the Si surface layer. For the case of ISE SOI structures, after the capping layer is removed, the top layer is essentially single-crystal recrystallized silicon, from which CMOS circuits can be fabricated. The use of a buried insulator provides devices having higher speeds than can be obtained in conventional bulk material. Circuits containing in excess of 1.5 million CMOS transistors have been successfully fabricated in ISE material.

Figure 17B:
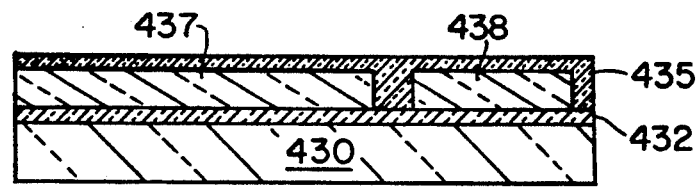
Figure 17C:
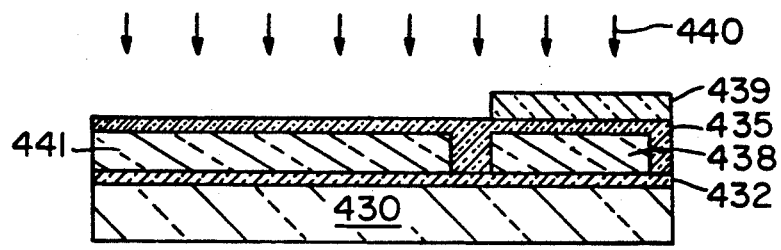
Figure 17D:
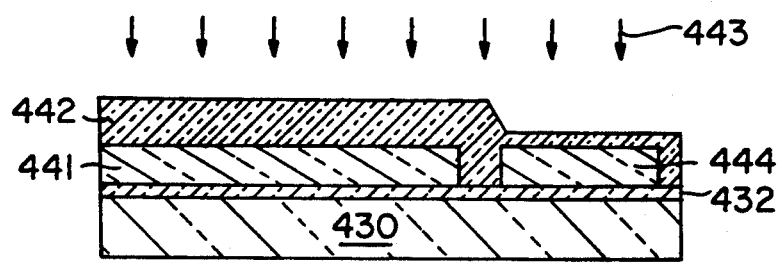

As shown in FIG. 17B, the silicon film 434 is patterned to define discrete islands 437 and 438 for each pixel. An oxide layer 435 is then formed over the patterned regions including channels 448 between the islands 437 and 438. A twin well diffusion process is then employed to form both p and n wells. To form n wells, silicon nitride islands 439 are formed to isolate those islands 438 designated to be p wells (FIG. 17C). The remaining islands 437 are subsequently implanted with an n-type dopant 440 to form n wells 441. To form p wells, a thick oxide layer 442 is grown over the n wells to isolate those islands from the p-type dopant 443, and the silicon nitride islands are removed (FIG. 17D). The non-isolated islands are then implanted with the p-type dopant 443 to form p wells 444.

Figure 17E:
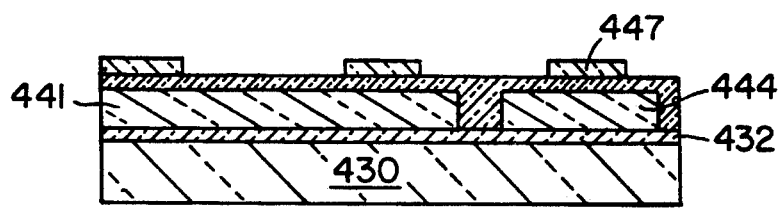
Figure 17F:
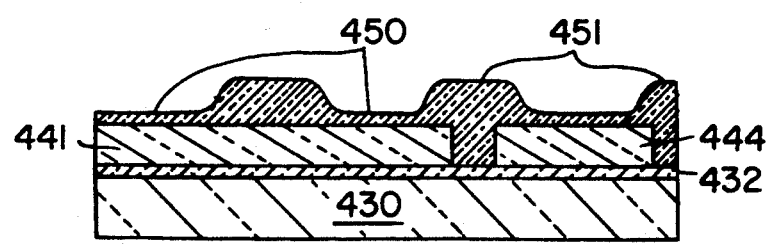
Figure 17G:
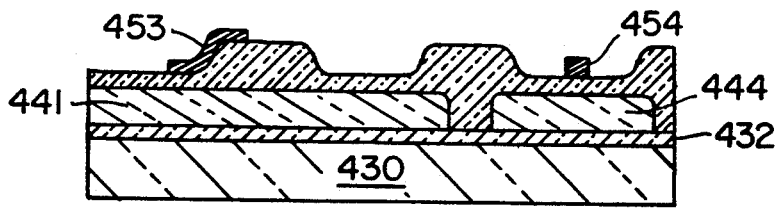

Following the twin well formation, a thick oxide film is grown over the surface of the silicon islands 441 and 444 to form active area regions. More specifically, the oxide layer 446 is etched to a relatively even thickness and silicon nitride islands 447 are deposited thereon (FIG. 17E). Next, a thick oxide film is grown around the surface of the silicon islands 441 and 444 to form active area regions 450 between the thick LOCOS field oxide regions 451 (FIG. 17F). Polysilicon is then deposited and patterned to form the gates 453 of the high voltage DMOS devices and the gates 454 of the low voltage CMOS devices (FIG. 17G). Note that the gate 453 of the DMOS device extends from the active area region 450 over the field oxide region 451. The edge of the gate 453 which is over the active region 450 is used as a diffusion edge for the p-channel diffusion, while the portion of the gate which is over the field oxide region 451 is used to control the electric field in the n well drift region.

Figure 17H:
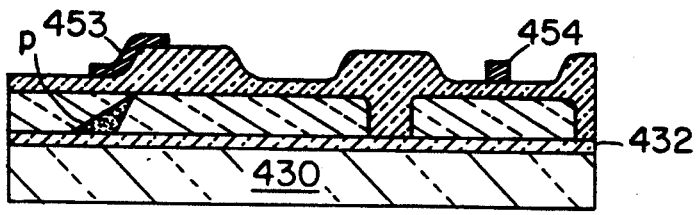
Figure 17I:
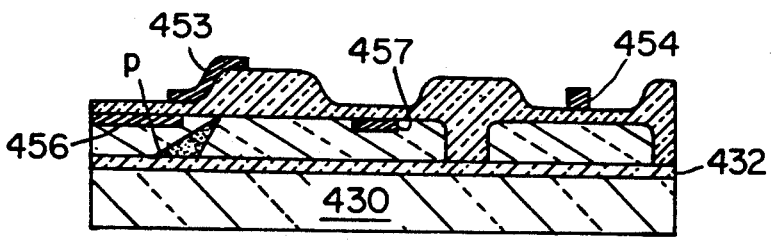
Figure 17J:
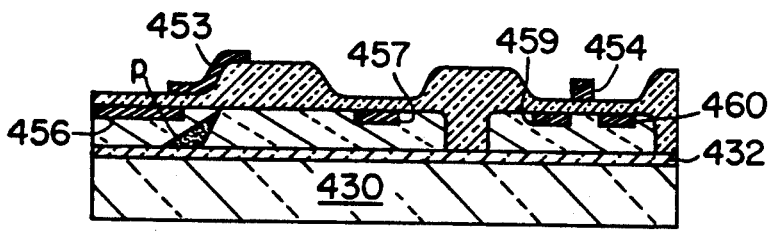

Following the channel diffusion, the n-channel and p-channel source 456, 459 and drain regions 457, 460 are formed using arsenic and boron implantation (FIGS. 17H-17J). Next, a borophosphorosilicate glass (BPSG) flow layer 458 is formed and openings are formed through the BPSG layer 458 to contact the source 456, the drain 457 and the gate 453 of the DMOS device as well as the source 459 and the drain 460 of the CMOS device (FIG. 17K). Further, a patterned metallization 462 of aluminum, tungsten or other suitable metal is used to connect the devices to other circuit panel components. The preferred process comprises nine masks and permits fabrication of both high voltage DMOS and low voltage CMOS devices.

The high voltage characteristics of the DMOS devices depend on several dimensions of the structure as well as the doping concentrations of both the diffused p-channel and n-well drift region. The important physical dimensions are the length of the n-well drift region, the spacing between the edge of the polysilicon gate in the active region and the edge of the underlying field oxide, and the amount of overlap between the polysilicon gate over the field oxide and the edge of the field oxide. The degree of current handling in the DMOS devices is also a function of some of these parameters as well as a function of the overall size of the device. Since a preferred embodiment includes a high density array (1M pixels/in$^2$), the pixel area, and hence the transistor size, is kept as small as possible.

Referring to FIG. 17L, the circuit panel can optionally be removed from the substrate 430 and transferred to a glass plate 431 upon which EL phosphors have been formed. The removal process can comprise CEL, CLEFT or back etching and/or lapping as previously described in earlier embodiments.

FIGS. 18A-18D illustrate the details of the fabrication process of an electroluminescent color display. As stated earlier, this fabrication process is based on the EL color display formation process disclosed in internation application PCT/US88 01680 to Barrows et al. incorporated herein by reference. The EL display formation process, whether for a monochrome or color display, comprises the sequential deposition of layers of an emissive thin-film stack. The phosphor layers are patterned such that each color pixel includes red, green and blue phosphor elements. The red color is obtained by filtering a yellow ZnS:Mn phosphor layer so as to only select the red component. The green and blue phosphor elements have components other than Mn for emitting in the desired spectral regions.

Figure 18A:
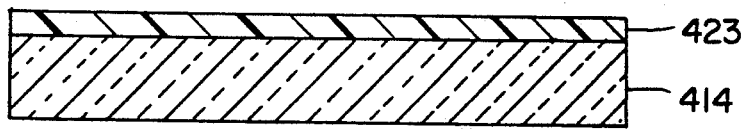
FIGS. 18A–18D is preferred process flow sequence illustrating the fabrication of an electroluminescent color display.
Figure 18B:
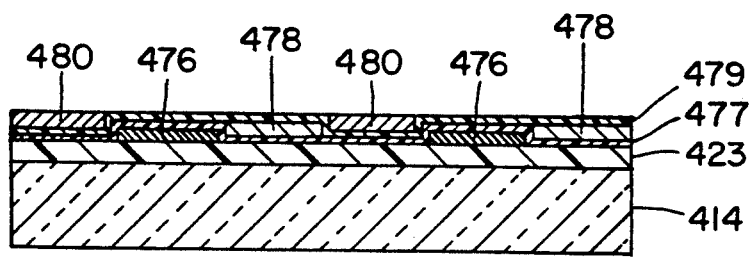

The first layer of the EL display is the bottom electrode. In a preferred EL display formation process, the bottom electrode comprises the source or drain metallization of the transistor in the drive circuit. This electrode may be optimized for high reflection of the desired wavelength to increase the luminous efficiency of the EL panel. Referring to FIG. 18A, the fabrication process begins with the deposition of the bottom insulator 423, preferably covering the entire surface of the active matrix of the circuit panel 414. The first color phosphor layer 476 is then deposited onto the active matrix and patterned. A first etch stop layer 477 is deposited, and a second color phosphor layer 478 is deposited and patterned over the stop layer (FIG. 18B). A second etch stop layer 479 is deposited, and a third color phosphor layer 480 is deposited and patterned over the second stop layer.

Figure 18C:
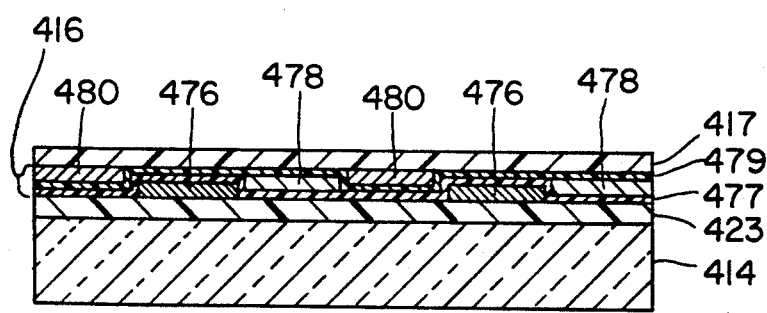
Figure 18D:
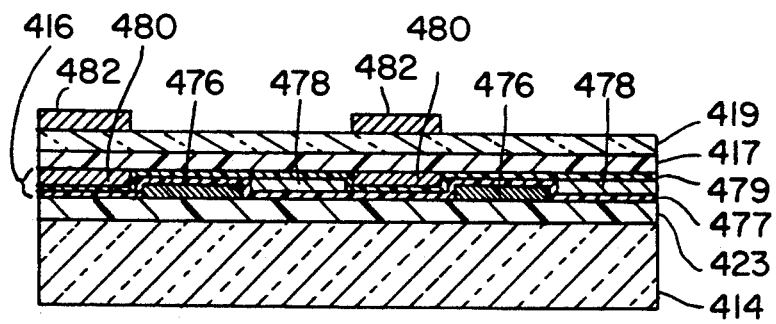

Referring to FIG. 18C, the array of patterned phosphor layers 416 is then coated with the top insulator 417. The two insulating layers 417 and 423 are then patterned to expose the connection points between the top electrodes and the active matrix circuit panel, and also to remove material from areas which external connections will be made to the drive logic. The top electrode 419 formed of an optically transparent material such as indium tin oxide is then deposited and patterned over the top insulator 417 (FIG. 18D). The deposition of the top electrode serves to complete the circuit between the phosphors 416 and the active matrix circuitry 414. A red filter 482 is then deposited and patterned over the red pixels, or alternatively is incorporated on a seal cover plate if a cover is used. The red filter 482 transmits the desired red portion of the ZnS:Mn phosphor (yellow) output to produce the desired red color.

Alternatively, the EL thin-film stack may be formed on a glass or other substrate to which the active matrix circuit panel is transferred by the aforementioned transfer processes. Yet another option comprises the transfer of both the circuit panel and the EL stack to another material such as a curved surface of a helmet-mounted visor.

Figure 19A:
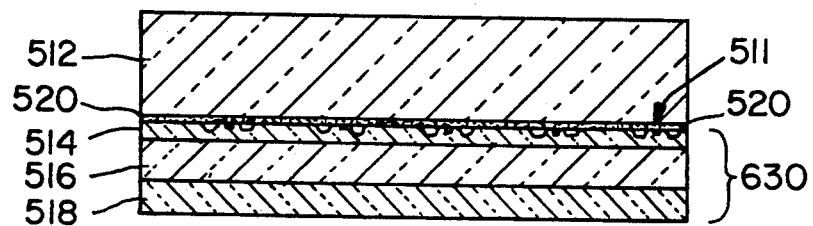
FIGS. 19A–19B is a preferred process flow sequence illustrating transfer and bonding of an SOI structure to a superstrate and removal of the substrate.
Figure 19B:
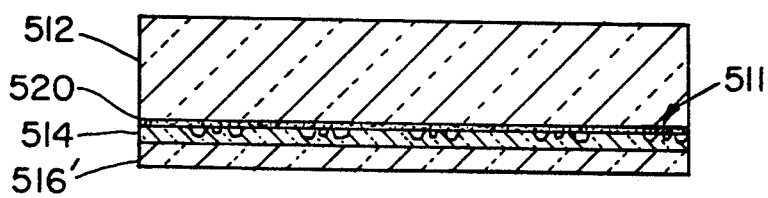

A preferred process for transferring and adhering thin-films of silicon from its support substrate to a different material is illustrated in FIGS. 19A–19B. This process may be employed for transferring a circuit panel formed in thin-film silicon (FIGS. 17A–17L) or an entire EL display (FIGS. 18A–18D) and adhering it to a different material such as glass or a curved surface of a material.

Referring to FIG. 19A, the starting structure is a silicon wafer 500 upon which an oxide layer 516 an a thin film of single crystal silicon 514 is formed using any of the previously described techniques, such as ISE or CLEFT. A plurality of circuits 511 such as pixel electrodes, TFTs, drivers and logic circuits are then formed in the thin-film silicon 514. The SOI processed wafer is then attached to a superstrate 512, such as glass or other transparent insulator or a curved surface of a material, using an adhesive 520.

The wafer is then cleaned and the native oxide is etched off the back surface 518. The wafer is put into a solution (KOH or equivalent). The etchant has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the etcher to observe the process and to stop in the buried oxide layer 516' without punching through to the thin silicon layer 514 above it. Wafers up to 25 mils thick and oxides as thin as 4000 Å have been successfully etched using this process. An alternative etchant is hydrazine which has a different etch rate selectivity.

The thin film 514 transferred to the glass 512 is now rinsed and dried. If not already provided with the circuitry 511, it can be backside circuit processed. Also, if desired, the film can be transferred to another substrate and the glass superstrate can be etched off, allowing access to the front side of the wafer for further circuit processing.

Figure 20A:
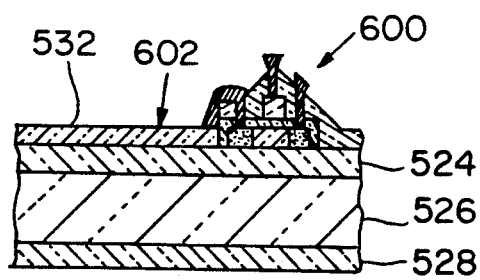
FIGS. 20A–20B is a preferred process flow sequence illustrating an alternative transfer process in which a GeSi alloy is used as an intermediate etch stop layer.
Figure 20B:
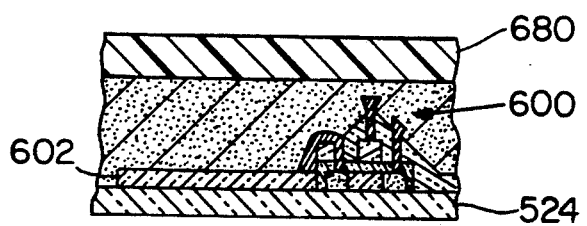

FIGS. 20A–20B illustrate an alternative silicon thin-film transfer process in which GeSi is used as an intermediate etch stop layer. Referring to FIG. 20A, in this process, a silicon buffer layer 526 is formed on a single crystal silicon substrate 528 followed by a thin GeSi layer 524 and a thin single crystal silicon device or circuit layer 532; using well-known CVD or MBE growth systems.

The layer 532 is then IC processed in a manner previously described to form circuits such as TFTs 600 or pixel electrodes 602. Next, the processed wafer is mounted on a glass or other support 680 using an epoxy adhesive. The epoxy fills in the voids formed by the previous processing and adheres the front face to the superstrate 680.

Next, the original silicon substrate 528 and the silicon buffer 526 are removed by etching with KOH, which does not affect the GeSi layer 524 (FIG. 20B). Finally, the GeSi layer 524 is selectively etched away which does not affect the silicon film 522.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims.

We claim:

1. A method of fabricating a panel display comprising:
   a) forming a silicon-on-insulator structure including a single thin film layer of essentially single crystal silicon material on an insulating layer, the insulating layer being positioned over a semiconductor substrate;
   b) forming an array of transistors in or on the single layer of essentially single crystal silicon material to form a circuit panel, the circuit panel including an array of display pixel electrodes such that each display pixel electrode is actuatable by at least one transistor; and
   c) positioning an electroluminescent material over each display pixel electrode such that an electric field generated at each display pixel electrode causes light to be emitted by the electroluminescent material.

2. The method of claim 1 wherein the essentially single crystal silicon is a thin film formed over a silicon substrate.

3. The method of claim 1 wherein step a) comprises:
   forming a non-single crystal semiconductor material; and
   crystallizing the non-single crystal semiconductor material to form the essentially single crystal silicon material.

4. The method of claim 3 wherein the crystallizing step is followed by the step of forming the array of transistors in the layer of essentially single crystal silicon material.

5. The method of claim 3 further comprising forming a drive circuit in or on the layer of essentially single crystal silicon material such that each transistor is electrically connected to the drive circuit.

6. The method of claim 1 further comprising positioning an optically transmissive electrode array over the electroluminescent material such that the electric field generated at each display pixel lies between an optically transmissive electrode and a pixel electrode.

7. The method of claim 1 further comprising transferring the layer of essentially single crystal silicon material from the semiconductor substrate onto an optically transmissive substrate.

8. The method of claim 7 wherein the transferring step comprises the step of removing the semiconductor substrate from the layer of essentially single crystal silicon material.

9. The method of claim 8 wherein the removing step comprises chemically etching the semiconductor substrate from the layer of essentially single crystal silicon material.

10. The method of claim 7 wherein the layer of essentially single crystal silicon material is transferred onto a curved surface of the optically transmissive substrate.

11. The method of claim 7 wherein the transferring step further comprises bonding the circuit panel to the optically transmissive substrate.

12. The method of claim 1 wherein the transistors are formed from single crystal silicon.

13. A method of fabricating an electroluminescent panel display comprising:
    forming a layer of polycrystalline silicon on an insulating substrate;
    forming a capping layer over the polycrystalline silicon;
    scanning the polycrystalline silicon layer with a heat source to crystallize the polycrystalline silicon layer and form a single thin film layer of single crystal silicon;
    forming an array of display pixels in or over the single crystal silicon, each display pixel comprising a circuit having at least one transistor;
    forming an electroluminescent material positioned over each display pixel such that an electric field applied to the material by the display pixel alters a light emitting property of the material; and
    forming a driver circuit electrically connected to the circuit panel to actuate the display pixels.

14. A method of fabricating an electroluminescent panel display comprising:
    a) forming a layer of essentially single crystal silicon material over an insulating layer, the insulating layer being positioned over a semiconductor substrate;
    b) forming an array of transistor circuits in the layer of essentially single crystal silicon material to form a circuit panel of display pixels wherein each pixel comprises an associated transistor circuit within the array of transistor circuits such that each display pixel is actuatable by the associated transistor circuit; and
    c) positioning a plurality of layers of electroluminescent material over the circuit panel of display pixels, the plurality of layers including layers having different colors such that an electric field generated by the associated transistor circuit for a display pixel causes an emission of light by the layers of electroluminescent material.

15. The method of claim 14 further comprising transferring the layer of essentially single crystal silicon material from the supporting substrate onto an optically transmissive substrate.

16. The method of claim 15 wherein the layer of essentially single crystal silicon material is transferred onto a curved surface of the optically transmissive substrate.

17. The method of claim 16 wherein the transferring step further comprises bonding the circuit panel to the optically transmissive substrate.

18. The method of claim 14 further comprising positioning an optically transmissive material over the electroluminescent material is forming an array of optically transmissive electrodes each being associated with a display pixel of the circuit panel.

19. The method of claim 18 wherein the optically transmissive material comprises indium tin oxide.

20. The method of claim 14 wherein the transferring step comprises removing the semiconductor substrate by chemically etching it from the layer of essentially single crystal silicon material.

21. The method of claim 14 wherein the essentially single crystal silicon material comprises single crystal silicon and further comprising forming a drive circuit with the layer of single crystal silicon such that each transistor circuit is electrically connected to the drive circuit.

22. The method of claim 21 wherein the drive circuit comprises CMOS logic devices.

23. The method of claim 14 wherein step a) comprises:
    forming a non-single crystal on the insulating layer; and
    crystallizing the non-single crystal to an essentially single crystal material.

24. A method of fabricating a panel display comprising:
    forming a layer of essentially single crystal silicon material on an insulating layer, the insulating layer being over a semiconductor substrate;
    forming an array of transistors in or on the layer of essentially single crystal silicon material to form a circuit panel of display pixels such that each display pixel is actuatable by at least one transistor;
    transferring the layer of essentially single crystal silicon material from the semiconductor substrate to a panel substrate; and
    positioning an electroluminescent material over each display pixel such that an electric field or signal generated at each display pixel causes light emission by the electroluminescent material.

25. The method of claim 24 wherein the step of forming a layer of essentially single crystal silicon material comprises:
    forming a non-single crystal semiconductor material; and
    crystallizing the non-single crystal semiconductor material to form the essentially single crystal silicon material.

26. The method of claim 24 wherein the panel substrate is an optically transmissive substrate.

27. The method of claim 24 wherein the panel substrate is a curved surface.

28. The method of claim 24 wherein the step of transferring comprises adhering the layer of essentially single silicon material to the panel substrate using an adhesive.

* * * * *